(12) United States Patent
Cumming

(10) Patent No.: US 7,276,329 B2
(45) Date of Patent: Oct. 2, 2007

(54) METHOD OF SORTING CELLS

(75) Inventor: Ian Cumming, Axminster (GB)

(73) Assignee: Ovasort Limited, Monmouth (GB)

( * ) Notice: Subject to any disclaimer, the term of this patent is extended or adjusted under 35 U.S.C. 154(b) by 0 days.

(21) Appl. No.: 10/221,241

(22) PCT Filed: Mar. 8, 2001

(86) PCT No.: PCT/GB01/00982

§ 371 (c)(1),
(2), (4) Date: Dec. 6, 2002

(87) PCT Pub. No.: WO01/68226

PCT Pub. Date: Sep. 20, 2001

(65) Prior Publication Data

US 2003/0175917 A1 Sep. 18, 2003

(30) Foreign Application Priority Data

Mar. 14, 2000 (GB) ................................ 0006051.7

(51) Int. Cl.
*A01N 1/00* (2006.01)
*A61B 17/43* (2006.01)
(52) U.S. Cl. ............................................. 435/2; 600/33
(58) Field of Classification Search .................... 435/2; 600/33

See application file for complete search history.

(56) References Cited

U.S. PATENT DOCUMENTS

| | | | |
|---|---|---|---|
| 3,816,249 A | * | 6/1974 | Bhattacharya .................. 435/2 |
| 4,083,957 A | | 4/1978 | Lang |
| 4,092,229 A | | 5/1978 | Bhattacharya |
| 4,225,405 A | | 9/1980 | Lawson |

OTHER PUBLICATIONS

Ijaz et al. Journal of Dairy Science. 1989, vol. 72, No. 10, pp. 2683-2690.*
Balerna et al. "Human Sperm Processing". Prog. Reprod. Biol. Med., 1994, vol. 16, pp. 45-75.*
Manger et al. "Effect of sperm motility on separation of bovine x- and Y- bearing spermatozoa by means of free-flow electrophoresis" *ANDROLOGIA*, vol. 29, No. 1, Jan. 1997-Feb. 1997pp. 9-15.
Ishijima et al. "Zeta potential of human x- and y-bearing sperm" *International Journal of Andrology*, vol. 14, No. 5, Oct. 1991, pp. 340-347.
Engelmann et al. "Separation of human x and y spermatozoa by free flow electrophoresis" *Gamete Research*, vol. 19, No. 2, 1998, pp. 151-160.
Blottner et al. "Enrichment of bovine x and y spermatozoa by free-flow electrophoresis" *Journal of Veterinary Medicine Series A*, vol. 41, No. 6. Aug. 1994, pp. 466-474.

* cited by examiner

*Primary Examiner*—Vera Afremova
(74) *Attorney, Agent, or Firm*—Bret E. Field; Bozicevic, Field & Francis LLP

(57) ABSTRACT

A method of sorting cells, particularly, but not exclusively, sperm cells, is described. The method comprises the use of a surface decontamination medium to strip the cells of any extra-cellular surface contamination and to then subject to stripped cells to a charge based separation.

16 Claims, 20 Drawing Sheets

| ATP content (pg/ml.) | Concentration of ATP Standard (0.96 mg/ml.) | Reading 1. RLU. | Reading 2. RLU. | Mean Reading. RLU. |
| --- | --- | --- | --- | --- |
| 96000000 | 1:10 | 1182315 | 1180305 | 1181310 |
| 9600000 | 1:100 | 1281789 | 1281618 | 1281703.5 |
| 960000 | 1:1000 | 981900 | 985632 | 983766 |
| 480000 | 1:2000 | 667618 | 687093 | 677355.5 |
| 240000 | 1:4000 | 420853 | 411804 | 416328.5 |
| 120000 | 1:8000 | 239502 | 239369 | 239435.5 |
| 60000 | 1:16000 | 123478 | 123326 | 123402 |
| 30000 | 1:32000 | 61625 | 66429 | 64027 |
| 15000 | 1:64000 | 31164 | 32421 | 31792.5 |
| 7500 | 1:128000 | 15993 | 16724 | 16358.5 |
| 3750 | 1:256000 | 11438 | 11141 | 11289.5 |
| 1875 | 1:512000 | 4384 | 4154 | 4269 |
| 937.5 | 1:1240000 | 3290 | 3122 | 3206 |
| 468.75 | 1:2480000 | 1772 | 1757 | 1764.5 |

FIG. 2

| Bull A Sperm/ml. | Dilution rate | RLU | Bull B. Sperm/ml. | Dilution rate. | RLU |
|---|---|---|---|---|---|
| 79 | (1:1953125) | 43 | 56 | (1:1953125) | 70 |
| 397 | (1:390625) | 84 | 282 | (1:390625) | 98 |
| 1984 | (1:78125) | 326 | 1408 | (1:78125) | 259 |
| 9920 | (1:15625) | 1002 | 7040 | (1:15625) | 952 |
| 49600 | (1:3125) | 4395 | 25200 | (1:3125) | 4217 |
| 248000 | (1:625) | 23032 | 176000 | (1:625) | 22648 |
| 1240000 | (1:125) | 73659 | 880000 | (1:125) | 109836 |
| 6200000 | (1:25) | 233747 | 4400000 | (1:25) | 408733 |
| 31000000 | (1:5) | 497871 | 22000000 | (1:5) | 747221 |

FIG. 3

Table 13.

| Bull B. Sperm/ml | RLU | Sperm dilution |
|---|---|---|
| 75000000 | 426112 | 1:1 |
| 15000000 | 127276 | 1:5 |
| 3000000 | 29067 | 1:25 |
| 600000 | 6204 | 1:125 |
| 120000 | 1352 | 1:625 |
| 24000 | 291 | 1:3125 |

Table 14.

| Bull A. Sperm/ml | RLU | Sperm dilution. |
|---|---|---|
| 12500000 | 352107 | 1:1 |
| 2500000 | 54446 | 1:5 |
| 500000 | 15127 | 1:25 |
| 100000 | 3490 | 1:125 |
| 20000 | 866 | 1:625 |
| 4000 | 294 | 1:3125 |
| Bull B Sperm/ml | RLU | Sperm dilution. |
| 6500000 | 140943 | 1:1 |
| 1300000 | 30171 | 1:5 |
| 260000 | 7655 | 1:25 |
| 52000 | 1763 | 1:125 |
| 10400 | 476 | 1:625 |
| 2080 | 165 | 1:3125 |

Table 15.

| Bull B. Sperm/ml | RLU | Sperm dilution |
|---|---|---|
| 125000000 | 47944 | Raw |
| 25000000 | 32289 | 1:5 |
| 5000000 | 15577 | 1:25 |
| 1000000 | 4850 | 1:125 |
| 200000 | 1320 | 1:625 |
| 40000 | 359 | 1:3125 |

FIG. 4

| Fraction | Luke (RLU) | Fraction | Inquiry (RLU) |
|---|---|---|---|
| 1 | 1352 | 1 | |
| 3 | 2407 | 3 | |
| 5 | 2498 | 5 | |
| 7 | 4909 | 7 | |
| 9 | 10728 | 9 | |
| 11 | 15477 | 11 | |
| 13 | 23866 | 13 | |
| 15 | 36731 | 15 | |
| 17 | 58718 | 17 | |
| 19 | 70810 | 19 | |
| 21 | 93407 | 21 | |
| 23 | 124319 | 23 | |
| 25 | 186719 | 25 | 856 |
| 27 | 169418 | 27 | 1046 |
| 29 | 174993 | 29 | 1236 |
| 31 | 213558 | 31 | 2280 |
| 33 | 173954 | 33 | 2065 |
| 35 | 99138 | 35 | 1680 |
| 37 | 271354 | 37 | 2154 |
| 39 | 149381 | 39 | 6011 |
| 41 | 64086 | 41 | 18013 |
| 43 | 38131 | 43 | 8246 |
| 45 | 25924 | 45 | 5283 |
| 47 | 10974 | 47 | 5456 |
| 49 | 4915 | 49 | 3905 |
| 51 | 1983 | 51 | 2304 |
| 53 | 674 | 53 | 966 |
| 55 | 477 | 55 | 420 |

FIG. 5

| Fraction | Luke (RLU) | Fraction | Inquiry (RLU) |
|---|---|---|---|
| 1 | 4209 | 1 | |
| 3 | 4857 | 3 | |
| 5 | 4890 | 5 | |
| 7 | 10702 | 7 | |
| 9 | 22712 | 9 | 476 |
| 11 | 19016 | 11 | 1390 |
| 13 | 15321 | 13 | 4504 |
| 15 | 17719 | 15 | 13519 |
| 17 | 20117 | 17 | 19632 |
| 19 | 27261 | 19 | 65562 |
| 21 | 34406 | 21 | 111493 |
| 23 | 41959 | 23 | 147531 |
| 25 | 49513 | 25 | 183570 |
| 27 | 61985 | 27 | 320812 |
| 29 | 74454 | 29 | 458054 |
| 31 | 93239 | 31 | 512168 |
| 33 | 112025 | 33 | 566283 |
| 35 | 61362 | 35 | 372626 |
| 37 | 10700 | 37 | 178970 |
| 39 | 8703 | 39 | 276673 |
| 41 | 6706 | 41 | 374377 |
| 43 | 6885 | 43 | 206163 |
| 45 | 7065 | 45 | 37950 |
| 47 | 5794 | 47 | 22633 |
| 49 | 4524 | 49 | 7316 |
| 51 | 2039 | 51 | 3765 |
| 53 | 330 | 53 | 1425 |
| 55 | | 55 | 817 |

FIG. 6

| Fraction | Luke (RLU) | Fraction | Inquiry (RLU) |
|---|---|---|---|
| 5 |  | 5 | 997 |
| 7 |  | 7 | 1004 |
| 9 |  | 9 | 1012 |
| 11 |  | 11 | 1215 |
| 13 |  | 13 | 1419 |
| 15 |  | 15 | 1575 |
| 17 |  | 17 | 1732 |
| 19 |  | 19 | 1667 |
| 21 |  | 21 | 1603 |
| 23 |  | 23 | 1566 |
| 25 | 699 | 25 | 1530 |
| 27 | 1218 | 27 | 1158 |
| 29 | 1104 | 29 | 1855 |
| 31 | 4378 | 31 | 2390 |
| 33 | 9160 | 33 | 7245 |
| 35 | 24372 | 35 | 12682 |
| 37 | 404082 | 37 | 54517 |
| 39 | 142887 | 39 | 64899 |
| 41 | 83833 | 41 | 22291 |
| 43 | 32466 | 43 | 7351 |
| 45 | 15148 | 45 | 7124 |
| 47 | 4669 | 47 | 4080 |
| 49 | 2062 | 49 | 2264 |
| 51 | 1795 | 51 | 1952 |
| 53 | 1964 | 53 | 1822 |
| 55 | 1491 | 55 | 1320 |
| 57 | 1207 | 57 | 1346 |
| 59 | 1466 | 59 | 1085 |
| 61 | 1131 | 61 | 1209 |
| 63 | 1826 | 63 | 983 |
| 65 | 1108 | 65 | 910 |
| 67 | 1171 | 67 |  |
| 69 | 902 | 69 |  |

FIG. 7

Table 20.

FISH results for cells recovered from FFE fractions towards the anode.

| Bull | Fraction | Date | Control Signal. Sperm nos. | Control No Signal. Sperm nos. | Separated Signal. Sperm nos. | Separated No Signal. Sperm nos. | Chi-squared |
|---|---|---|---|---|---|---|---|
| Luke | 4 | 30.7.98 | 197 | 151 | 15 | 37 | p<0.01 |
| Luke | 6 | 30.7.98 | 189 | 146 | 1 | 1 | Insuff. Data |
| Luke | 8 | 30.7.98 | 245 | 197 | 2 | 3 | Insuff. Data |
| Luke | 10 | 5.8.98 | 131 | 162 | 1 | 5 | Insuff. Data |
| Luke | 12 | 5.8.98 | 116 | 134 | 1 | 0 | Insuff. Data |
| Luke | 13 | 5.8.98 | 203 | 156 | 0 | 0 | Insuff. Data |
| Luke | 14 | 5.8.98 | 221 | 219 | 0 | 0 | Insuff. Data |
| Luke | 31 | 3.9.98 | 171 | 221 | 3 | 21 | p<0.01 |
| | | Total. | 1473(51.5%) | 1386(48.5%). | 23(25.6%). | 67(74.4%). | p<0.01 |
| Inquiry | 3 | 5.8.98 | 153 | 152 | 18 | 29 | Not signif. |
| Inquiry + | Luke | Total. | 1626(51.4%). | 1538(48.6%). | 41(29.9%). | 96(70.1%). | p<0.01 |

FISH results from cells recovered from FFE fractions towards the cathode.

| Bull | Fraction | Date | Control Signal Sperm nos. | Control No Signal Sperm nos. | Separated Signal Sperm nos. | Separated No Signal Sperm nos. | Chi-squared |
|---|---|---|---|---|---|---|---|
| Luke | 51 | 30.7.98 | 177 | 200 | 76 | 47 | p<0.01 |
| Luke | 52 | 30.7.98 | 141 | 118 | 9 | 101 | p<0.01 |
| Luke | 44 | 5.8.98 | 164 | 177 | 156 | 102 | p<0.01 |
| Luke | 50 | 5.8.98 | 163 | 175 | 134 | 123 | Not signif |
| Luke | 52 | 5.8.98 | 151 | 173 | 138 | 71 | p<0.01 |
| Luke | 54 | 5.8.98 | 157 | 200 | 120 | 131 | Not signif |
| Luke | 49 | 3.9.98 | 140 | 163 | 45 | 102 | p<0.01 |
| Luke | 53 | 3.9.98 | 170 | 163 | 36 | 58 | p<0.05 |
| Luke | 63 | 3.9.98 | 127 | 149 | 3 | 3 | Insuff.Data |
| Luke | 67 | 3.9.98 | 162 | 168 | 8 | 19 | Not signif. |
| | | Total | 1552(47.9%). | 1686(52.1%). | 725(48.9%). | 757(51.1%). | Not signif |
| Inquiry | 49 | 5.8.98 | 169 | 167 | 87 | 208 | p<0.01 |
| Inquiry | 50 | 5.8.98 | 241 | 208 | 71 | 241 | p<0.01 |
| Inquiry | 52 | 5.8.98 | 143 | 147 | 46 | 72 | Not signif. |
| | | Total | 553(51.4%). | 522(48.6%). | 204(28.1%). | 521(71.9%). | p<0.01 |
| Inquiry + | Luke | Total | 2105(48.8%). | 2208(51.2%). | 929(42%). | 1278(58%). | p<0.01 |

FIG. 8

Table 21

FISH results from the laboratory of UNCEIA.

| Bull | Fraction | Date | Polarity | X-signal Separated No. sperm | Y-signal Separated No sperm | No signal Separated No.sperm | X-signal Control No.sperm | Y-signal Control No.sperm | No signal Control No sperm | Chi-squared |
|---|---|---|---|---|---|---|---|---|---|---|
| Inquiry | 60 | 26.8.98 | Cathode | 20 (57%) | 5 (14%) | 10 (29%) | 58 (47%) | 52 (42%) | 14 (11%) | p<0.05 |
| Inquiry | 61 | 26.8.98 | Cathode | 20 (61%) | 9 (27%) | 4 (12%) | 48 (48%) | 52 (52%) | Nil | p<0.05 |
| Luke | 44 | 27.8.98 | Cathode | 20 (69%) | 4 (14%) | 5 (17%) | 47 (48%) | 48 (49%) | 5 (5%) | p<0.01 |
| Luke | 69 | 26.8.98 | Cathode | 23 (96%) | 1 (4%) | Nil | 50% (assumed) | 50% (assumed) | | Binomial p<0.01 |

FIG. 9

METHOD OF SORTING CELLS

This invention relates to a method of sorting of cells. More particularly the present invention relates to a method of sorting cells using a charge based separation process.

It is desirable to be able to separate cells based on phenotypic differences, especially where the cells are related, for example to be able to separate pathogenic bacteria from a mixture of pathogenic and innocuous bacteria of the same genus, or cells of a pre-selected sub-population from a mixed population of cells, such as normal cells from mutated cells, or X-chromosome bearing sperm from an ejaculate. Many methods have been proposed, for example, using immunological techniques, using size or weight differences between cells, or using binding techniques such as affinity binding.

In the description which follows the present invention will be described with reference to its preferred application which is in the sorting of sperm cells, particularly mammalian sperm cells, but it is not intended at present that the invention be limited to this application since the method of cell separation employed finds equal utility in other cell sorting processes such as those described above.

The prior art describes many methods by which it is intended to effect separation of X- and Y-chromosome bearing sperm. For example, U.S. Pat. No. 4,722,887 describes the separation of sperm by use of an antibody directed to a sulfoglycolipid normally expressed on the cell surface.

Another example of prior art methods to effect sperm sorting is based on the belief that that the X-bearing sperm cell is physically larger than the Y-bearing cell, on the grounds that the X-chromosome contains more DNA than the Y-chromosome, and that this will consequently increase overall cell volume in X-chromosome bearing cells. Hence, U.S. Pat. No. 5,514,537 describes the separation of X- and Y-chromosome bearing sperm using glass beads having different pore sizes, the Y-bearing sperm being able to penetrate a smaller pore size in the bead than the larger X-bearing sperm.

Many scientists believe that the only consistently identifiable difference between X- and Y-chromosome bearing mammalian sperm is that the X chromosome is physically bigger than the Y. Additionally, it is known that X-chromosome bearing cells contain more DNA in their nuclei than Y-bearing cells. As a result, when sperm cells are stained with a fluorescent DNA specific dye, the X-bearing cells will fluoresce slightly more intensively than Y-bearing cells. A machine has been devised (a fluorescence activated cell sorter or FACS), which can detect these differences in fluorescence and separate sperm cells with efficiencies of around 90% for both X- and Y-chromosome bearing cells. This approach is currently being developed commercially on an international basis.

The present inventor has found that genes on the Y-chromosome bearing cells are responsible for elements of sperm membrane formation essential for normal sperm development and fertility in both X- and Y-chromosome bearing cells. A physiological mechanism for transferring this essential Y-specific information to X-bearing cells during spermatogenesis has been postulated by the present inventor, the mechanism must ensure that the X-bearing cells can also use this information in order that the X-bearing cells may develop normally. The fact that such a mechanism exists is shown by the fact that in the absence of such a mechanism the X-bearing cells would otherwise be completely unable to provide this information for themselves, as they lack a Y-chromosome.

The present inventor is the first to recognise the implications of this new information for X- and Y-bearing sperm separation. Without wishing to be bound by theory, the present inventor believes that the mechanism of Y-specific information sharing between Y- and X-bearing cells is not 100% efficient, and that within every ejaculate there will be a very small population of X-bearing cells which will lack some (or all) of this Y-specific information.

Using this knowledge it is possible to separate X- and Y-chromosome bearing sperm. The present inventor has found that this information sharing results in a difference in the surface charge on the cell membrane.

Accordingly, the present invention provides a method of sorting cells, particularly, but not exclusively sperm cells, the method comprising the steps of treating the cells to remove extra-cellular surface contamination and subjecting the treated cells to a charge-based separation process.

The term "extra-cellular surface contamination" as used herein is intended to include all extra-cellular material which is not an intrinsic part of the cell membrane, particularly material which is added to or picked up by the cell after it has been formed. Hence, in the preferred embodiment of the separation of sperm cells, the term is intended to include the accessory proteins, sugars or other physiological material added to the cells during spermatogenesis, together with any other added secretions or additives, including micro-organisms (especially pathogens such as the HIV virus) acquired during the processes of cell membrane assembly, cellular maturation, cell storage, cell surface coating, cellular secretions or any other component of the ejaculatory fluid other than the sperm cell.

The surface charge of a cell is determined by the membrane protein content of the cell membrane. Hence, a method of sorting cells according to surface charge, that is the charge on the cell membrane, presents no insult to the genetic material carried by the cell and thus the risk of mutagenesis of the genetic material of the cell is minimised.

This is an important advantage over the methods of the prior art where the risk of mutagenesis is increased due to the insult applied to the cell by either the separation process or the cell identification process. Where such an insult is applied to the cell, especially a sperm cell, the desirability of the use of that cell in an in vitro fertilisation procedure is reduced by virtue of the unknown effect of the insult on the offspring. For example, the fluorescence activated cell sorting (FACS) known from the prior art is potentially dangerous due to the insult presented to the DNA (once stained, the cells are excited to fluoresce with a laser light source which is potentially damaging to DNA), and many scientists (in particular within the medical profession) are very concerned about using the technology. There is at present therefore, an unquantifiable risk of genetic defect for progeny born using this technology. Additionally, the technique is expensive since the cells need to be individually sorted.

Hence the reduction of this risk achieved when using the method of the present invention is advantageous and this is particularly important when the sperm is to be used in human IVF programmes or in pedigree livestock.

Preferably, the surface contamination removed is all of the extra-cellular material adhering to or bathing the cells. For example in sperm cells it is preferred that all of the ejaculatory fluid is removed from the sperm cells. However, it may be sufficient that the accessory proteins, such as spermadhesin, added to the sperm cells are removed. It is also desirable that the endogenous cell membrane properties, such as the net surface charge and membrane viability, are maintained during the removal of the cell-surface contaminants.

The surface contamination may be removed by the use of a cell-stripping medium such as a buffered solution comprising protein-, fat- or fatty acid-based additive which prevents or attenuates cell death while allowing the removal of the extra-cellular material. A preferred surface contamination removal medium comprises egg yolk or derivatives thereof. Preferably, the medium comprises up to 30% egg yolk or derivatives by volume, ideally 20% egg yolk or derivatives thereof by volume. It is preferred that the egg yolk is from chicken eggs although the use of eggs from other animals, particularly ducks or geese, is also contemplated.

The most preferred medium for the removal of cell surface contamination is the TEST-yolk medium described by Ijaz and Hunter (Ijaz, A., Hunter, A. G. and Graham, E. F. (1989). Induction of Bovine Sperm Capacitation by TEST-Yolk Semen Extender. Journal of Dairy Science. 72, 2683-2690.)

An advantage of the use of the TEST-yolk medium is that cell senescence is delayed.

It is a feature of the present invention that the separation of cells is effected according to their surface charge. In this respect it is preferred that separation is carried out using an electrophoretic process. More particularly it is preferred that the separation is effected using an electrophoretic process conducted in a mobile liquid medium. The term "mobile liquid medium" as used herein is intended to mean a liquid medium that has low viscosity or has not been gelled, or has a viscosity or an extent of gelling such that there is little or no impedance to the electrophoretic migration of the sperm cells.

It is also preferred that the electrophoretic conditions employed are constant throughout the separation chamber, that is that the conditions needed for reliable electrophoretic separation include the maintenance of constant running conditions. Preferably, the running conditions are absolutely constant and further include the use of measures to remove the heat induced by the electric field and to prevent turbulence and thermoconvection as a result of temperature differences, together with an operational temperature sufficiently low to render the cells immotile but not dead or damaged. Ideally, therefore, the electrophoretic process used in the present invention is a free flow electrophoresis process.

Surprisingly, the present inventor has found that mammalian sperm cells taken from both the anodic and the cathodic extremes of the electrophoresis chamber are only X-chromosome bearing sperm cells. According to the teaching of the prior art (Kaneko, S., Iizuka, R., Oshiro, S., Nakajima, H., Oshio, S. and Mohri H. (1983). Separation of Human X and Y-bearing sperm using Free-Flow Electrophoresis. Proceedings of the Japanese Academy. 59, Series B. 276-279. Kaneko, S., Oshio, S., Kobayashi, T., Iizuka, R. and Mohri H. (1984). Human X and Y-bearing Sperm Differ in Cell Sialic Acid Content. Biochemical and Biophysical Research Communications. 124, No. 3. 950-955. Mohri, H., Oshio, S and Kaneko, S. (1986). Sexing of Mammalian Sperm. Progress in Developmental Biology, Part A. 179-182. Ishijima, S. A., Okuno, M. and Mohri, H. (1991). Zeta Potential of Human X and Y-Bearing Sperm. International Journal of Andrology. 14, 340-347. Ishijima, S. A., Okuno, M., Odagiri, H., Mohri, T. and Mohri, H. (1992). Separation of X and Y-bearing Murine Sperm by Free-Flow Electrophoresis: Evaluation of Separation by PCR. Zoological Science. 9, 601-606.) X-bearing sperm can be isolated from a collection peak towards the anode, and Y-bearing sperm from a collection peak towards the cathode. However, the following workers have claimed to isolate X-bearing sperm from a peak towards the cathode, and Y-bearing sperm from a peak towards the anode by using Free-Flow Electrophoresis (Engelmann, U., Krassnig, F., Schultz, H and Schill, W. B. (1988). Separation of Human X and Y-bearing Spermatozoa by Free-Flow Electrophoresis. Gamete Research. 19, 151-159. Blottner, S., Bostedt, H., Mewes, K and Pitra, C. (1994). Enrichment of Bovine X and Y Spermatozoa by Free-Flow Electrophoresis. Journal of Veterinary Medicine. A. 41, 466-474. Manger, M., Bostedt., H., Schill, W. B. and Blottner, S. (1992). Influence of Sperm Motility on the Selective Isolation of Bovine X and Y-Spermatozoa by Free-Flow Electrophoresis. Proceedings of the 12th International Conference on Animal Reproduction. The Hague. Vol. 1. 493-495. Manger, M., Bostedt, H., Schill, W. B. and Mileham, A. J. (1997). Effect of Sperm Motility on Separation of Bovine X and Y-bearing Spermatozoa by Means of Free-Flow Electrophoresis. Andrologia. 29, 9-15.).

The reliable separation of X-chromosome bearing cells is useful in agriculture where it is desirable to be able to produce all female progeny, for example in pig breeding where it has been shown that females grow faster than males or for a dairy herd. Moreover, the production of all-female progeny for herd replacement, especially in cattle, would eliminate the production of large numbers of unwanted males (which is currently leading to welfare problems associated with the disposal of unwanted stock), for example for a dairy herd. Additionally, if the sorted sperm are used in conjunction with a human IVF programme, it will be possible to reduce the incidence of sex-linked diseases such as haemophilia or muscular dystrophy by guaranteeing that only daughters, who at worst will be carriers rather than sufferers, are produced as a result of in vitro fertilisation.

Although problems of loss of sperm motility have been identified in the prior art by using electrophoretic techniques, low yields of sperm which is reliably sorted according to sex is not envisaged as being problematical when combined with an IVF method such as intra cytoplasmic sperm injection (ICSI) where a single sperm is injected directly into an egg. It is in fact sufficient for this method to be able to use a single dead sperm and hence any loss of motility or cell death of the sperm is not seen to be particularly detrimental when using a cell of known sex identity.

In another aspect therefore, the present invention provides a method of producing female embryos, the method comprising the steps of treating sperm cells to remove extra-cellular surface contamination, subjecting the treated sperm cells to a charge-based separation process to separate the X- and Y-chromosome bearing sperm cells, and using X-chromosome bearing sperm cells separated thereby to fertilise an egg.

Accordingly, the present invention also encompasses embryos produced using this method. Ideally, all the embryos will be female.

Preferably, to produce an embryo, an egg is fertilised, using an IVF technique, using sperm separated according to the present invention. However, it is not intended to exclude the possibility that intra-vaginal artificial insemination techniques may be carried out using sperm separated by the method of the present invention. Most preferably, an egg is fertilised using an ICSI technique and is allowed to develop to a stage where the embryo can be frozen in accordance with general practice in this field.

BRIEF DESCRIPTION OF THE DRAWINGS

Embodiments of the invention will now be described by way of example only with reference to the appended drawings, of which

FIG. 2 is a table showing standard ATP concentrations and corresponding bioluminescent readings at different dilution rates;

FIG. 3 is a table showing sperm concentration and bioluminescence data (Relative Light Units) for bulls A and B;

FIG. 4 shows the sperm concentration and bioluminescence data (Relative Light Units) for bulls A and B;

FIG. 5 shows electrophoretic profile data for sperm from bulls Luke and Inquiry prepared in TEST-yolk (8:2) and stored for 24 hours; (Fractions 4(1305 RLU), 5(2498 RLU), 6(4524 RLU), 8(6882 RLU), 49(4915 RLU), 50(3449 RLU), 51(1983 RLU) and 52(802 RLU) were taken from Luke for FISH analysis. Fractions 25(856 RLU), 29(1236 RLU), 30(1758 RLU), 31(2280 RLU), 50(3104 RLU), 51(2304 RLU), 52(1635 RLU) and 53 (966 RLU) were taken from Inquiry for Fish analysis.)

FIG. 6 shows electrophoretic profile data for sperm from bulls Luke and Inquiry prepared in TEST-yolk (8:2) and stored for 24 hours; (Fractions 10(945 RLU), 12(292 RLU), 13(4505 RLU), 14(7809 RLU), 49(7316 RLU), 50(4403 RLU), 52(2013 RLU), 54(1061 RLU) were taken from Luke for FISH analysis. Fractions 1(4209 RLU), 2(4533 RLU), 3(4857 RLU), 4(4873 RLU), 49(4524 RLU), 50(2954 RLU), 51(2039 RLU) and 52(658 RLU) were taken from Inquiry for Fish analysis.)

FIG. 7 shows electrophoretic profile data for sperm from bulls Luke and Inquiry prepared in TEST-yolk (8:2) and stored for 24 hours; (Fractions 26(958 RLU), 27(1218 RLU), 29(1104 RLU), 31(4378 RLU), 49(2062 RLU), 53(1964 RLU), 63(1108 RLU) and 67(1171 RLU) were taken from Luke for FISH analysis. Fractions 9(1012 RLU), 27(1158 RLU), 29(1855 RLU), 31(2390 RLU), 49(2264 RLU), 51(1952 RLU), 53(1822 RLU) and 62(1096 RLU) were taken from Inquiry for Fish analysis.)

FIG. 8 shows FISH results for cells recovered from FFE fractions towards a) the anode and b) the cathode;

FIG. 9 shows the FISH results from the laboratory of UNCEIA;

Sperm Preparation for Initial FFE Optimisation

Figure 1:
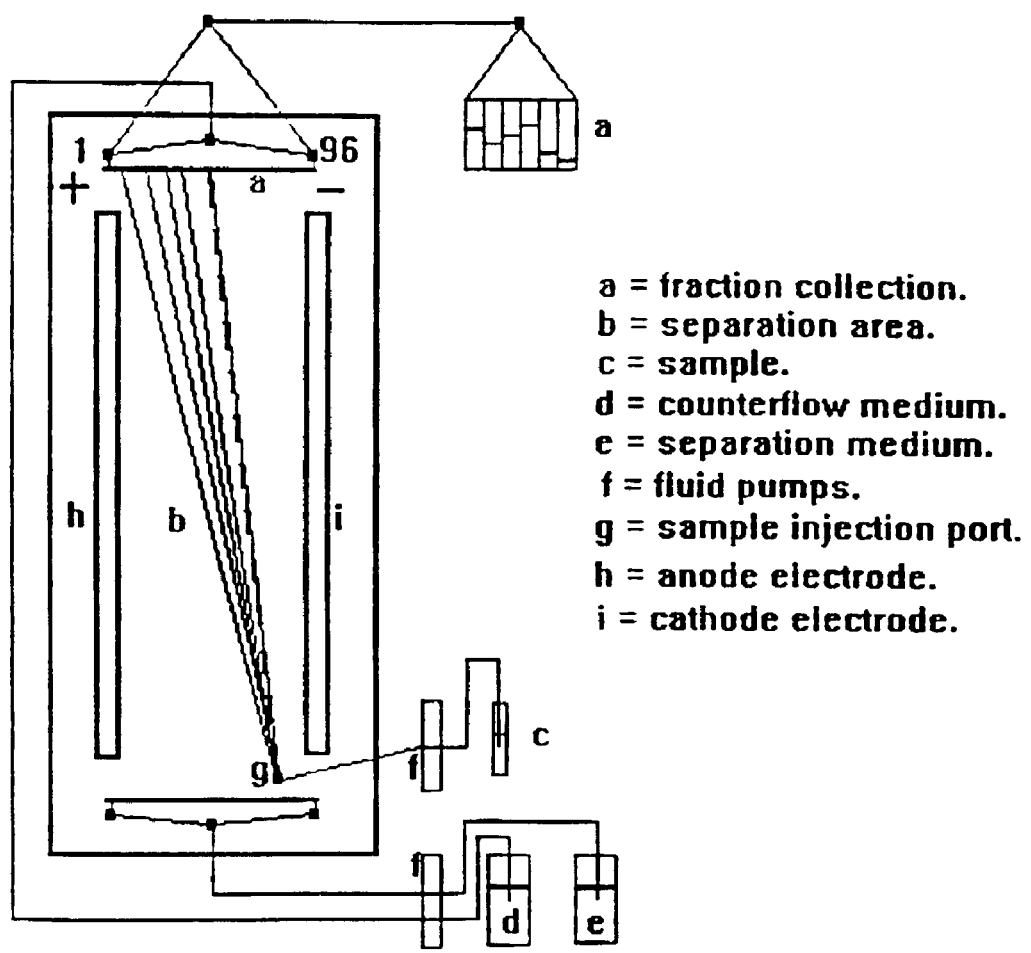
FIG. 1 shows schematically the free flow electrophoresis apparatus used in the method of the present invention.
Figure 10:
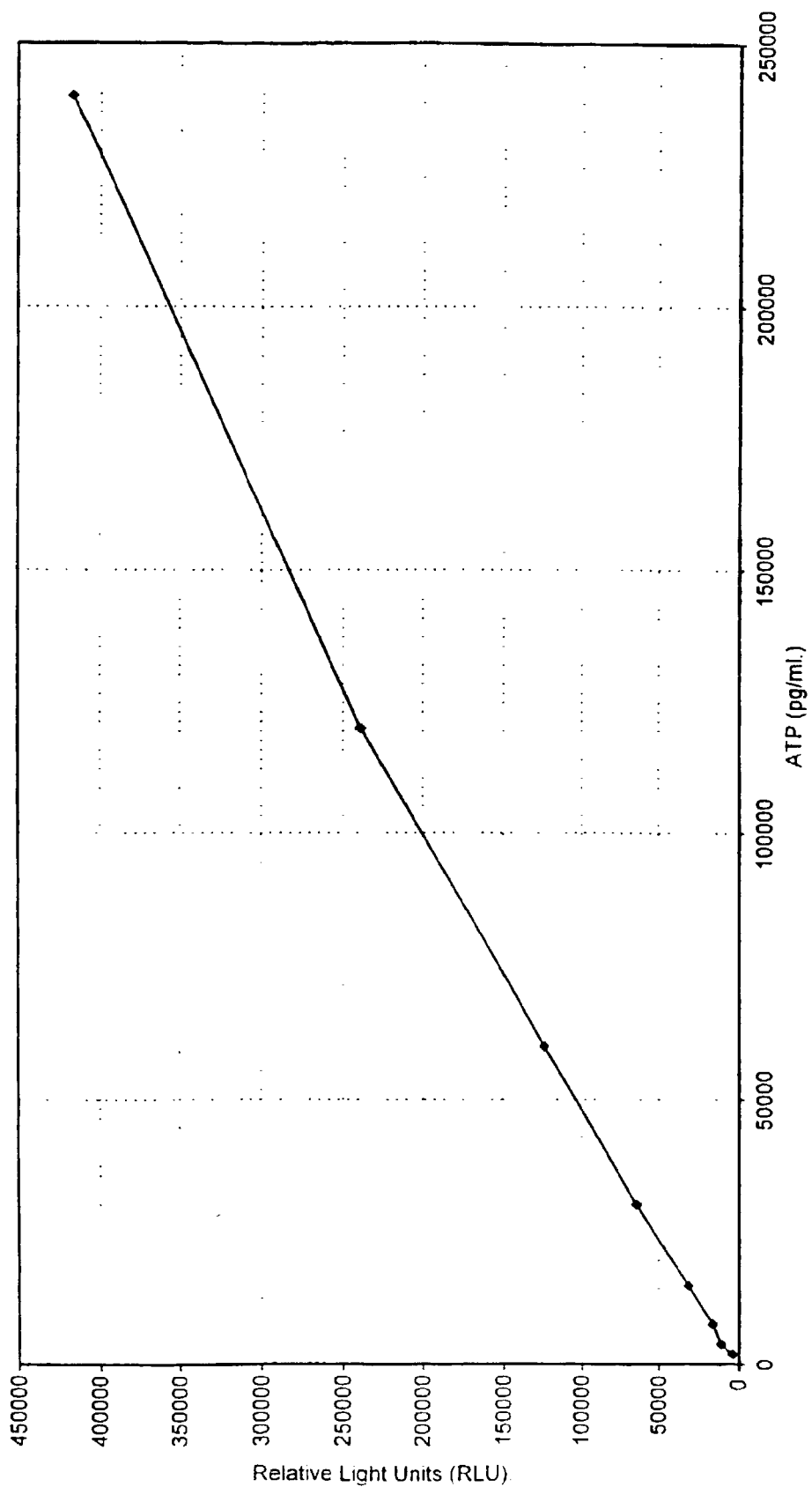
FIG. 10 is a graph showing the relationship between the concentration of ATP (pg/ml) and the intensity of chemiluminescence (RLU)

Semen was collected from two bulls standing at the Dartington Cattle Breeding Centre, Dartington, Totnes, Devon during routine centre collection for freezing and storage. Bulls "A" and "B" were used for this work.

Sperm Separation Using FFE

Semen samples were repeatedly collected over an eight week period from two bulls standing at Avoncroft Sires Ltd., Sugarbrook, Stoke Prior, Bromsgrove, Worcester B60 3AS during routine stud semen collection for freezing and storage.

FFE analysis was performed at the laboratories of the Leatherhead Food Research Association and semen samples were transported from Avoncroft in refrigerated containers either by courier or by Ian Cumming.

Both bulls were Holstein Friesians named Luke and Inquiry. Freshly ejaculated semen was diluted with TEST-Yolk at a ratio of 8 cc:2 cc TEST-Yolk: raw semen, and held for 24 hours at 5° C. before being prepared for FFE using a simple washing procedure with Triethanolamine buffer.

Preparation of TEST-Yolk

TEST-Yolk was prepared as according to the method of Ijaz and Hunter (1989): 22.35 g. of Tes (Sigma-Aldrich Co. Ltd., Poole, Dorset, England) and 5.91 g. of Tris (Sigma-Aldrich Co. Ltd., Poole, Dorset, England) were dissolved in 300 ml. and 150 ml. of distilled water respectively. Tes was titrated against Tris to pH 7.00. Chicken egg yolk (20% vol/vol.) was added and the mixture gently shaken until the egg yolk was evenly mixed. The mixture was then centrifuged at 12,000 g for 10 minutes and the supernatant fluid used for semen extension. The TEST-Yolk was stored for up to 2 months at −20° C. until used.

Sperm Washing

Separation media was prepared for the loading and transport of the sperm samples through the FFE machine (Octopus, Weber GmbH, Ismaning, Germany). The separation media consisted of a Triethanolamine buffer constituted as follows:

15 mM Triethanolamine (Fisher Scientific UK Ltd, Loughborough, England). 4 mM Potassium Acetate (Fisher Scientific UK Ltd.).

10 mM Glucose (Fisher Scientific UK Ltd.).

240 mM Glycine (Fisher Scientific UK Ltd.).

30 mM Sucrose (Fisher Scientific UK Ltd.).

Adjusted to pH 7.2-7.3 with acetic acid (Sigma-Aldrich Co. Ltd., Poole, England).

The simple sperm washing technique was performed as follows:

Three ml. of TEST-Yolk diluted semen was. added to 7 ml. of Triethanolamine buffer (separation media). This sample was then washed by centrifuging at 200 g for 5 minutes. The supernatant was aspirated down to the resultant sperm pellet and topped up to 10 ml. with Triethanolamine buffer. The sample was washed again by centrifuging at 200 g. for 5 minutes. The supernatant was again aspirated down to the sperm pellet and the sample was then topped up with 2 ml. of Triethanolamine buffer before using for FFE.

When required, 0.5 ml. of this suspension was held back for serial dilution analysis to estimate sperm density by using a haemocytometer.

This sperm preparation protocol was fully evaluated before using the Triethanolamine buffer for the sperm separations with FFE as follows:
1) Washed sperm samples were incubated in Triethanolamine buffer at 39° C. and 5% CO2 in air, at room temperature and at 5° C.
2) Samples were checked at regular intervals for sperm clumping and sperm motility.

FFE

The Octopus FFE machine was set up according to the manufacturer's instructions for Free-Flow Zone Electrophoresis. The stabilisation media (the buffer for stabilising the electric field around the chamber electrodes) was made up as follows:

45 mM Triethanolamine.
12 mM Potassium Acetate.
240 mM Glycine.          Adjusted to pH 7.2 with acetic acid.

The electrode buffer (the buffer inside the electrodes) was made up as follows:

150 mM Triethanolamine.
 40 mM Potassium Acetate.
240 mM Glycine.          Adjusted to pH 7.2 with acetic acid.

The electrical conditions in the electrophoresis chamber were set at 900 volts, 300 milliamps and 200 watts. Operating temperature in the chamber was set at 5° C.

The rate of sample injection into the chamber was set at 5.5 (arbitrary units). The rate of separation media flow in the FFE chamber was set at 2.0 (arbitrary units). The process of Free-Flow Zone Electrophoresis is represented diagrammatically in FIG. 1.

Fraction 1 was the fraction closest to the anode and fraction 96 was the fraction closest to the cathode. The sample injection port at the bottom of the chamber was aligned opposite collection fraction 76.

The initial commissioning of the machine was performed by a trained technician from Weber GmbH. Routine checks were subsequently made at regular intervals on the operational efficiency of the machine by using marker dyes carrying particles of pre-determined negative surface charge. The dyes were observed during their migration up the separation chamber to check that they adhered to pre-determined migration patterns.

During the FFE analysis the separation medium was injected via three ports at the base of the separation chamber. The separation medium was circulated evenly in a laminar flow system running from the bottom to the top of the separation chamber, and at right angles to the electric field created between the two chamber electrodes. A counterflow separation medium was injected at the top of the separation chamber and was controlled in such a way as to produce a "fluid barrier" at the level of the fraction collection ports. This produced a collection field at the top of the chamber which ensured undistorted fluid collection between fractions. The counterflow medium used was of identical constitution to the separation medium. The sample for FFE separation was injected from a single port positioned towards the cathode. Post injection through this port, charged cells then migrated freely in the electrical field towards the anode according to the degree of negative charge carried on their surface membranes, and the rate of separation media flow in the laminar flow system.

Individual cells were collected at the top of the separation chamber according to which of the 96 fraction collection ports they had migrated to. From each collection port, each fraction was pumped via a peristaltic pump to a collection vessel. The collection vessel consisted of a multiwell plate with a collection volume of 0.3 ml. per well and 96 wells.

Estimation of Sperm Density Per Collection Well/Tube

This was made using a system of ATP bioluminescence as described by Kyriakides and Patel (1994). Briefly, ATP bioluminescence is based on a reaction that occurs naturally in the North American firefly, *Photinus pyralis*. The reaction catalysed by the *Photinus* enzyme, luciferase, uses the chemical energy contained in the energy rich molecule ATP to drive the oxidative decarboxlyation of luciferin with the resultant production of light. Peak light output occurs within 0.3 seconds and because almost one photon of light is emitted for every ATP molecule consumed, a linear relationship exists between the concentration of ATP and light output, over a wide range of ATP concentrations. Reiger (1997) has shown that in bovine sperm samples, the measured ATP content as determined by bioluminescence, is directly proportional to the number of sperm in the sample. Since dead cells rapidly lose their ATP through autolysis, the level of ATP in a given sample is directly related to the number of living cells.

100 μl. aliquots from specified FFE collection fractions were individually analysed using the luciferin-luciferase reaction system and resultant light emission measured in a Biocounter M2500 photometer (Lumac Ltd., Batley, Yorkshire, England). Cells were permeabilized using Nucleotide Releasing Agent for Somatic ATP (Lumac Ltd.) and bioluminescence produced by using a Luciferin/Luciferase reagent mixture plus diluent; Lumit QM/Lumit QM diluent (Lumac Ltd.). Aliquots of pre-determined volumes of these reagents were injected automatically by the photometer into the collection fraction being analysed.

The photometer was calibrated using an ATP standard control (Sigma FL-AAS) known to contain 0.96 mg. of ATP per vial. 1 vial was diluted in 1 ml. of ATP buffer. Serial dilutions were then made and analysed for ATP bioluminescence. A graph was then plotted of bioluminescence (relative light units or RLU) against ATP concentration (pg/ml.).

A sample from a sperm suspension prepared for FFE was retained for serial dilution. A small drop from each dilution rate was assessed using phase contrast light microscopy at 100× magnification in order to select an appropriate sperm density for sperm counting using a haemocytometer (i.e., a density at which individual sperm could be clearly and easily counted). A sperm count was made at the appropriate dilution rate and used to estimate the sperm densities across the remaining serial dilution rates.

All serially diluted sperm samples were subsequently assessed for bioluminescence. A graph of bioluminescence against sperm density was plotted and subsequently used to estimate sperm densities as required, at different RLU values for sperm samples subjected to FFE.

The results from a bioluminescence analysis to estimate biomass start to become unreliable at cell densities of less than 10,000 cells/ml. (Patel, personal communication 1997).

Figure 15:
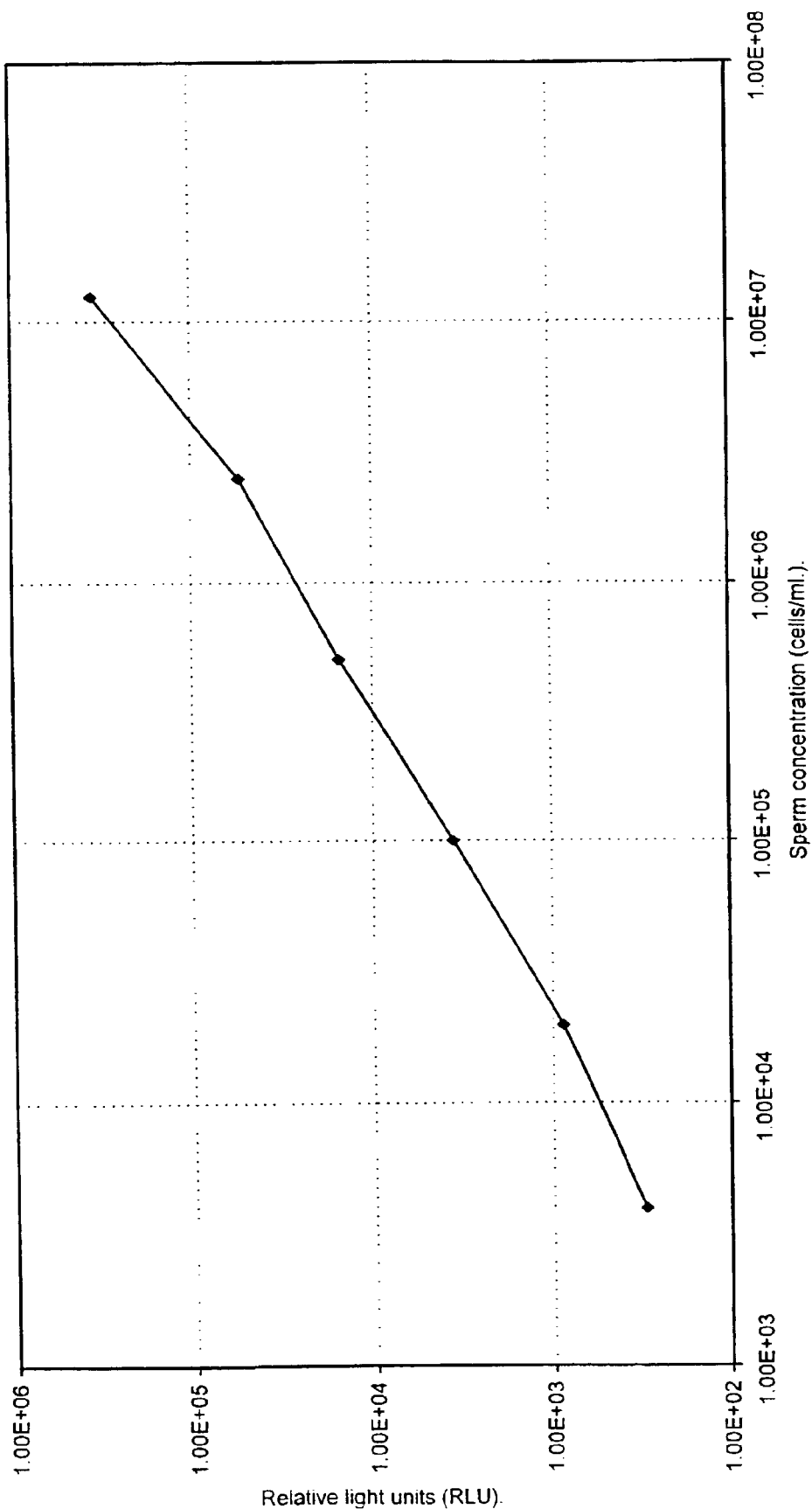
FIG. 15 is a graph showing ATP concentration (RLU) against bovine sperm count for bull A (24 hour sample)
Figure 16:
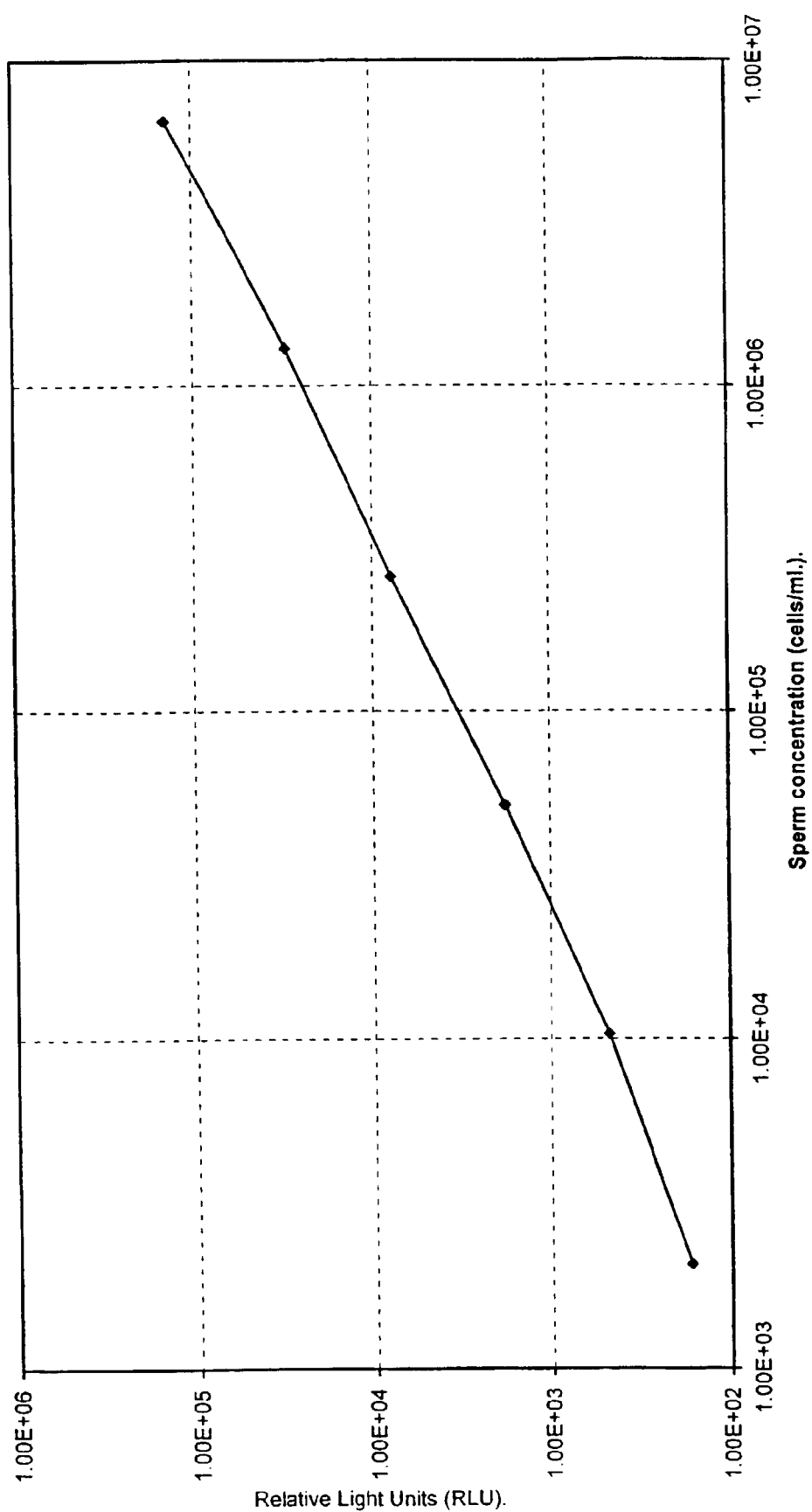
FIG. 16 is a graph showing ATP concentration (RLU) against bovine sperm count for bull B (24 hour sample)
Figure 17:
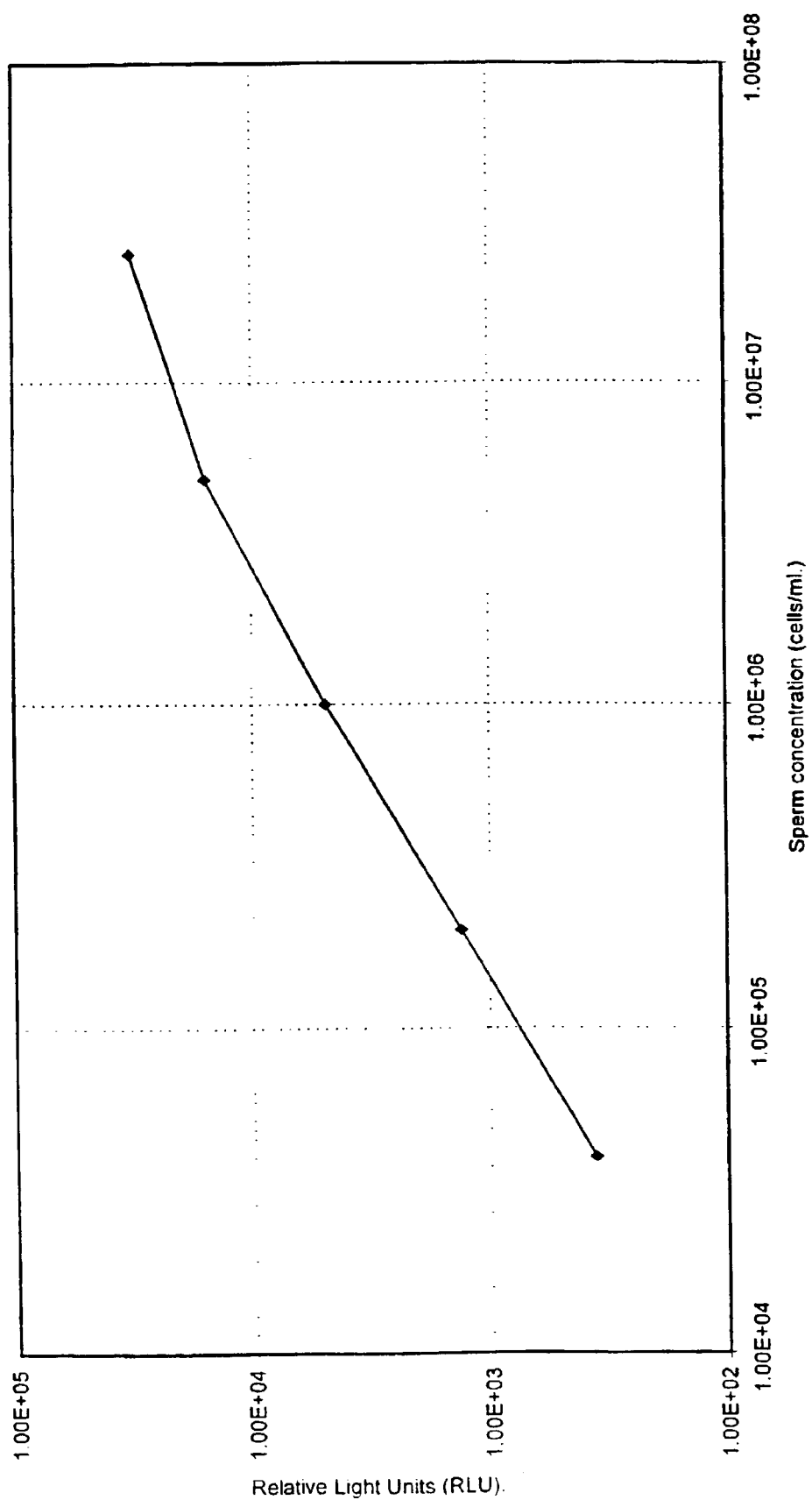
FIG. 17 is a graph showing ATP concentration (RLU) against bovine sperm count for bull A (48 hour sample)
Figure 18:
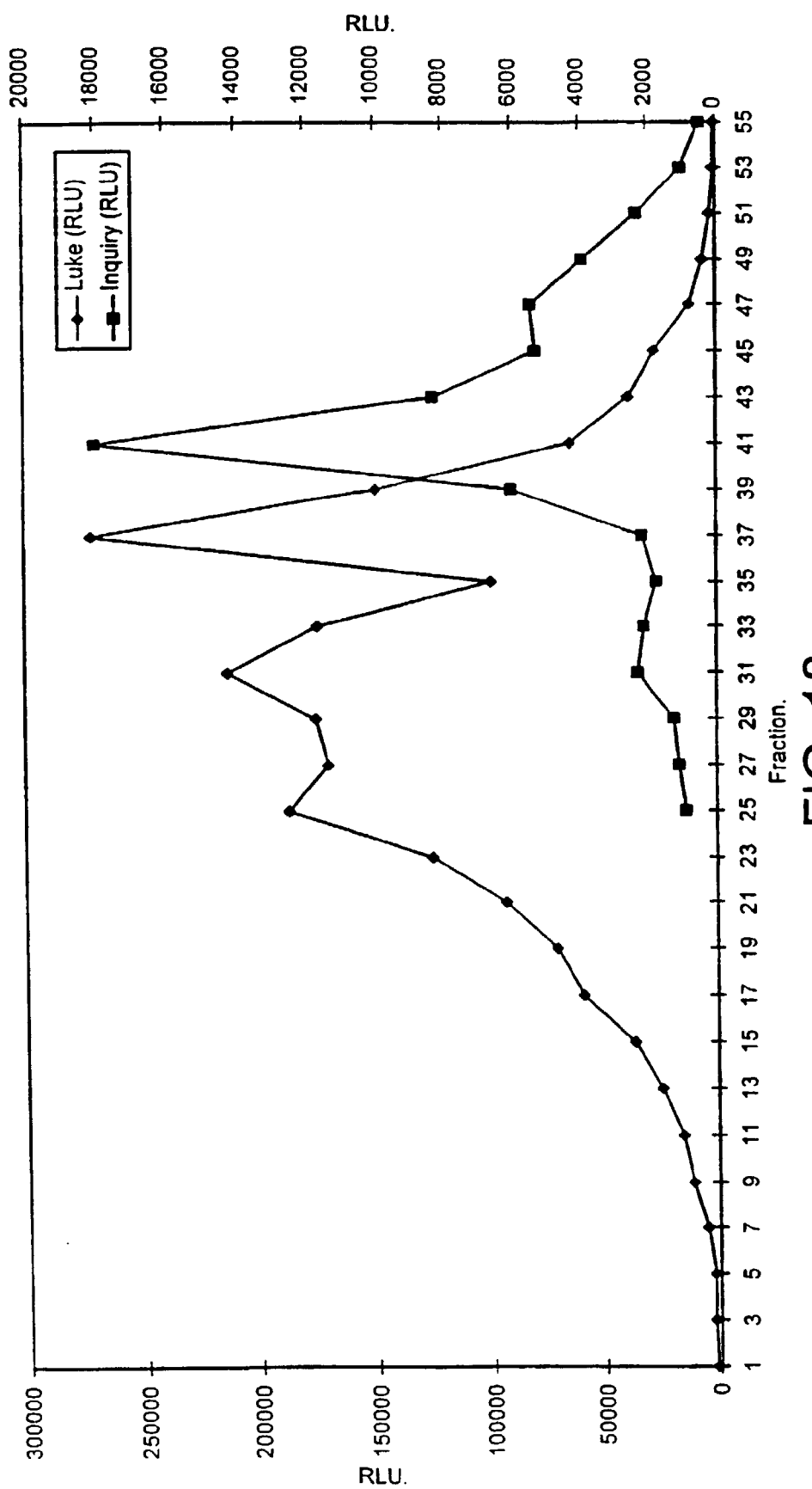
FIG. 18 is a graph showing FFE separation profiles for sperm samples from bulls Luke and Inquiry prepared in TEST-yolk (8:2) and stored for 24 hours.
Figure 19:
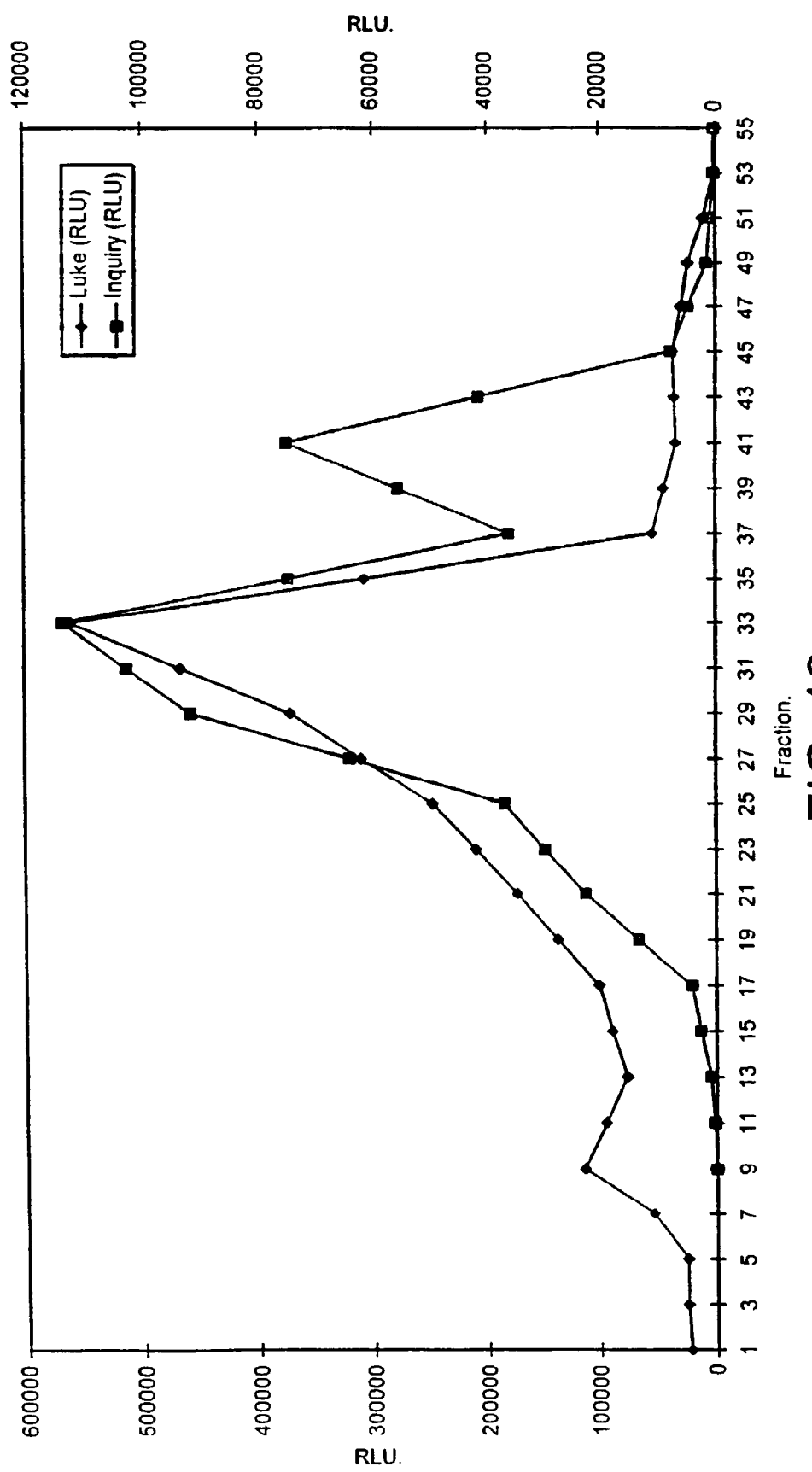
FIG. 19 is a graph showing FFE separation profiles for sperm samples from bulls Luke and Inquiry prepared in TEST-yolk and stored for 24 hours from a second batch.
Figure 20:
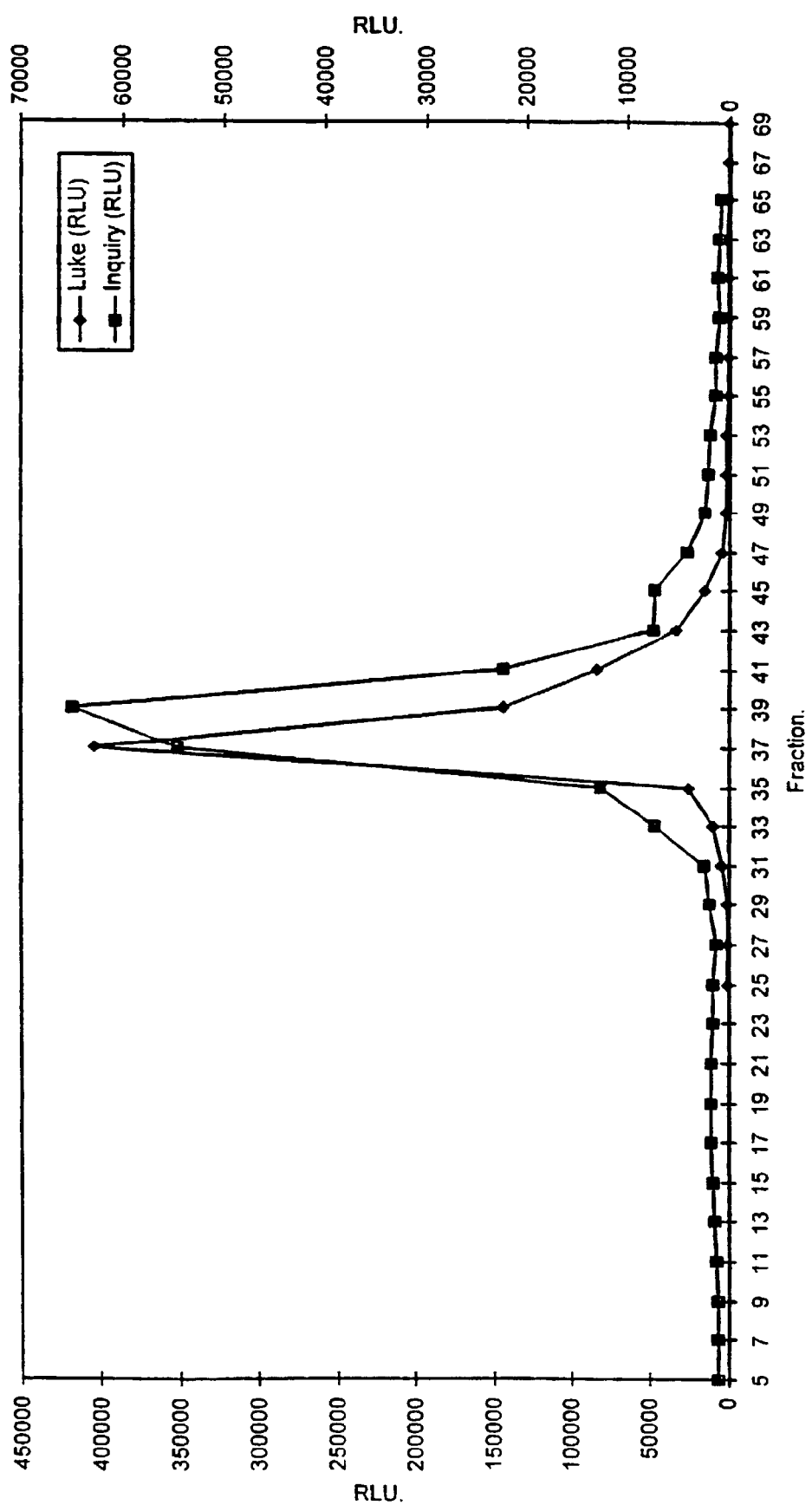
FIG. 20 is a graph showing FFE separation profiles for sperm samples from bulls Luke and Inquiry prepared in TEST-yolk and stored for 24 hours from a third batch.

At this level of cell density, levels of bioluminescence are too low for accurate photometric recording. For bulls A and B (FIGS. 15 and 16) cell densities of 10,000 cells/ml. corresponded to an RLU reading of no more than 500. Wherever possible therefore, fractions containing RLU readings of less than 500 RLU were not used in the interpretation of experimental results, nor were such samples taken for experimental analysis.

Estimation of ATP Content Per Sperm

By analysing the relationship between bioluminescence and both ATP concentration (standard) and sperm density, the relationship between sperm density and ATP concentration was calculated to estimate the ATP content per sperm. This was then compared with known published values to verify the accuracy and suitability of the bioluminescence technique.

Bioluminescence will only detect the ATP content of living cells, as dead cells rapidly lose ATP through autolysis. In order to establish the proportion of live cells in a sample, an Eosin-Nigrosin stain was performed on sperm samples as follows:

a) Five drops of Eosin-Nigrosin stain (Arthur C. Gurr Ltd., Leicester, England) were placed in a test tube and warmed in a waterbath at 37° C.
b) One drop of semen was added to the stain.
c) The tube contents were mixed well.
d) The tube contents were left to stand for one minute in a waterbath at 37° C.
e) One drop of the stained semen mixture was placed on a clean slide in order to make a smear which was then dried over a flame.
f) The slide was examined under oil×1000 and the live and dead cell numbers were counted.

Dead cells have damaged membranes which have become permeable and therefore will absorb the stain and appear pink. Live cells have impermeable membranes and therefore appear unstained.

Results

Suitability of Triethanolamine Buffer

After 5 hours incubation in Triethanolamine buffer, sperm samples at 39° C. and 5% CO2 in air, and at room temperature, showed good motility and slight clumping. After 5 hours at 5° C., sperm showed very poor motility with slight clumping. After 6 hours at 39° C. and 5% CO2 in air, motility started to reduce whist at 5° C. sperm were immotile. After 24 hours at 39° C. and 5% CO2 in air, sperm were immotile whilst at room temperature sperm were still weakly motile.

For the purposes of the FFE procedure, sperm were suspended in Triethanolamine buffer for between 1 and 2 hours maximum. Sample temperature was kept as close to 5° C. as possible during the procedure. On the basis of the above results, it was decided that Triethanolamine buffer would maintain sperm viability in the absence of significant sperm clumping for long enough for FFE to be fully evaluated.

Bioluminescence

Figure 13:
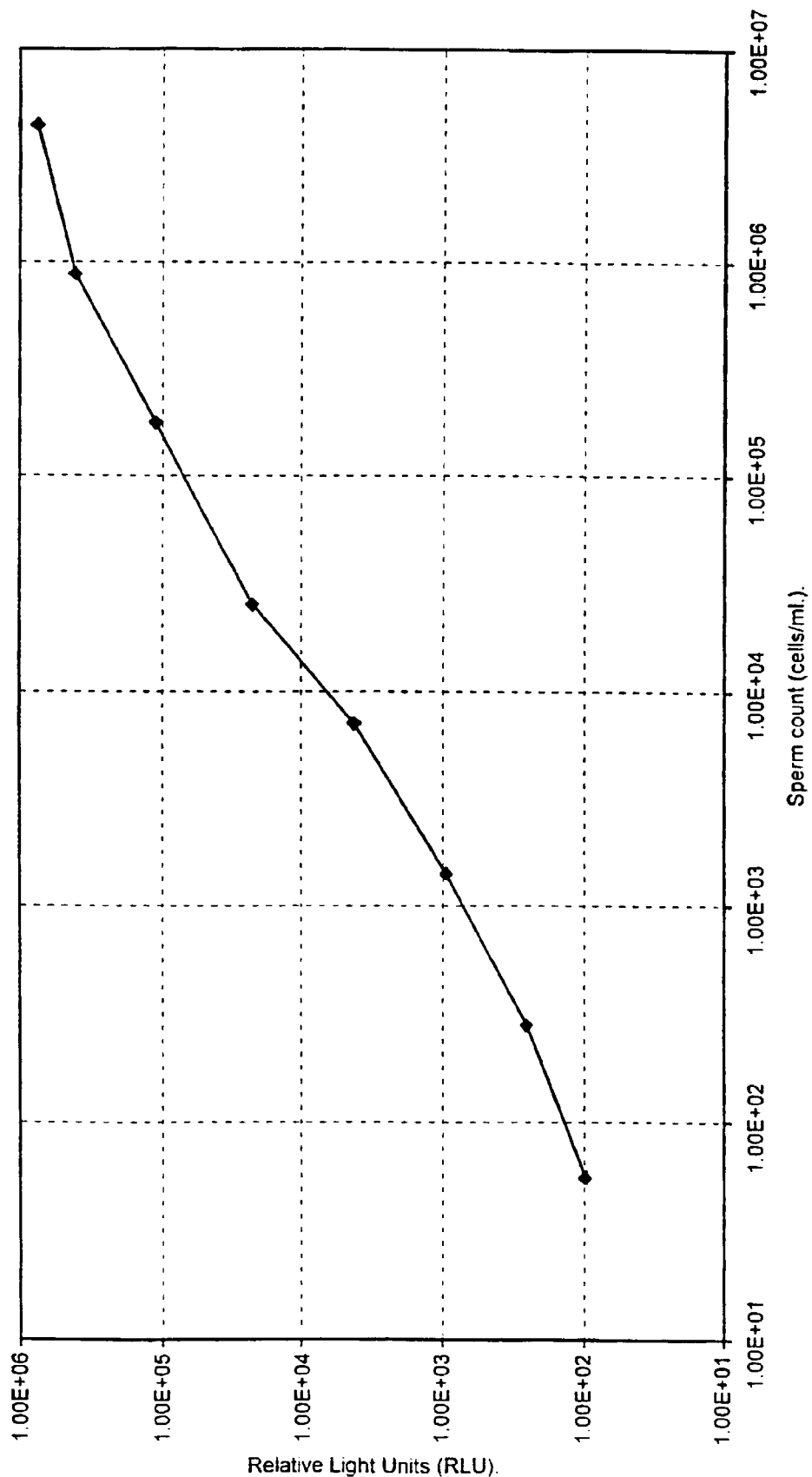
FIG. 13 is a graph showing ATP concentration against bovine sperm count for bull B.
Figure 14:
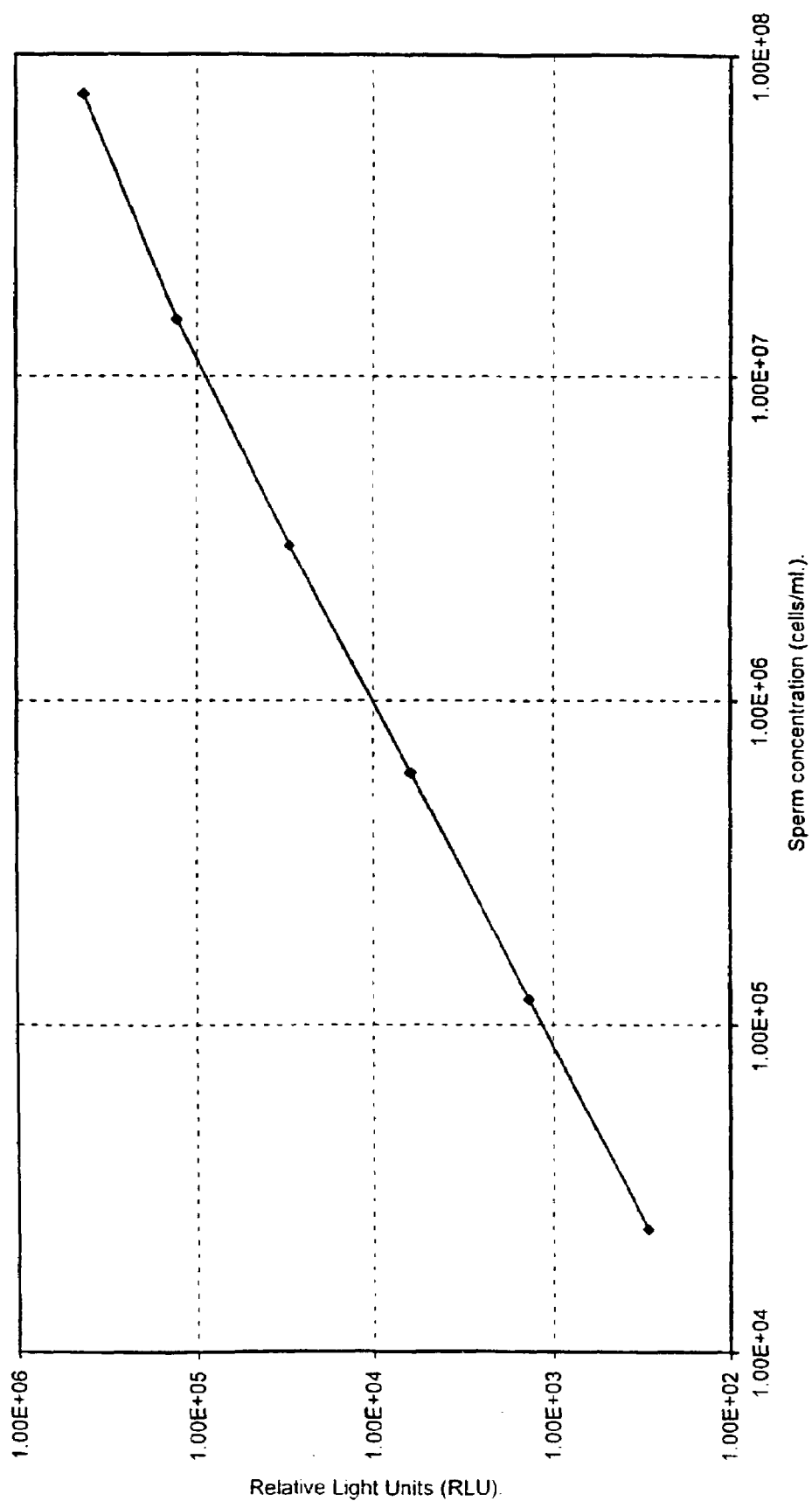
FIG. 14 is a graph showing ATP concentration (RLU) against bovine sperm count for bull B (48 hour sample)

The results of the calibration using the ATP standard and the photometer are represented in FIG. 2 and FIGS. 13 and 14. As expected, the relationship between bioluminescence (RLU) and ATP concentration, is linear.

The relationship between bioluminescence and sperm concentration for sperm samples analysed on 13.5.97, 11.6.97, 18.6.97 and 2.7.97 are shown in tables 12 to 15 and FIGS. 15 to 20 respectively. The relationship between RLU and sperm count is either linear or approaching linear. These graphs were used to estimate the sperm concentrations in the fractions at the extremes of the range of electrophoretic mobility.

ATP Concentration Per Sperm

Figure 11:
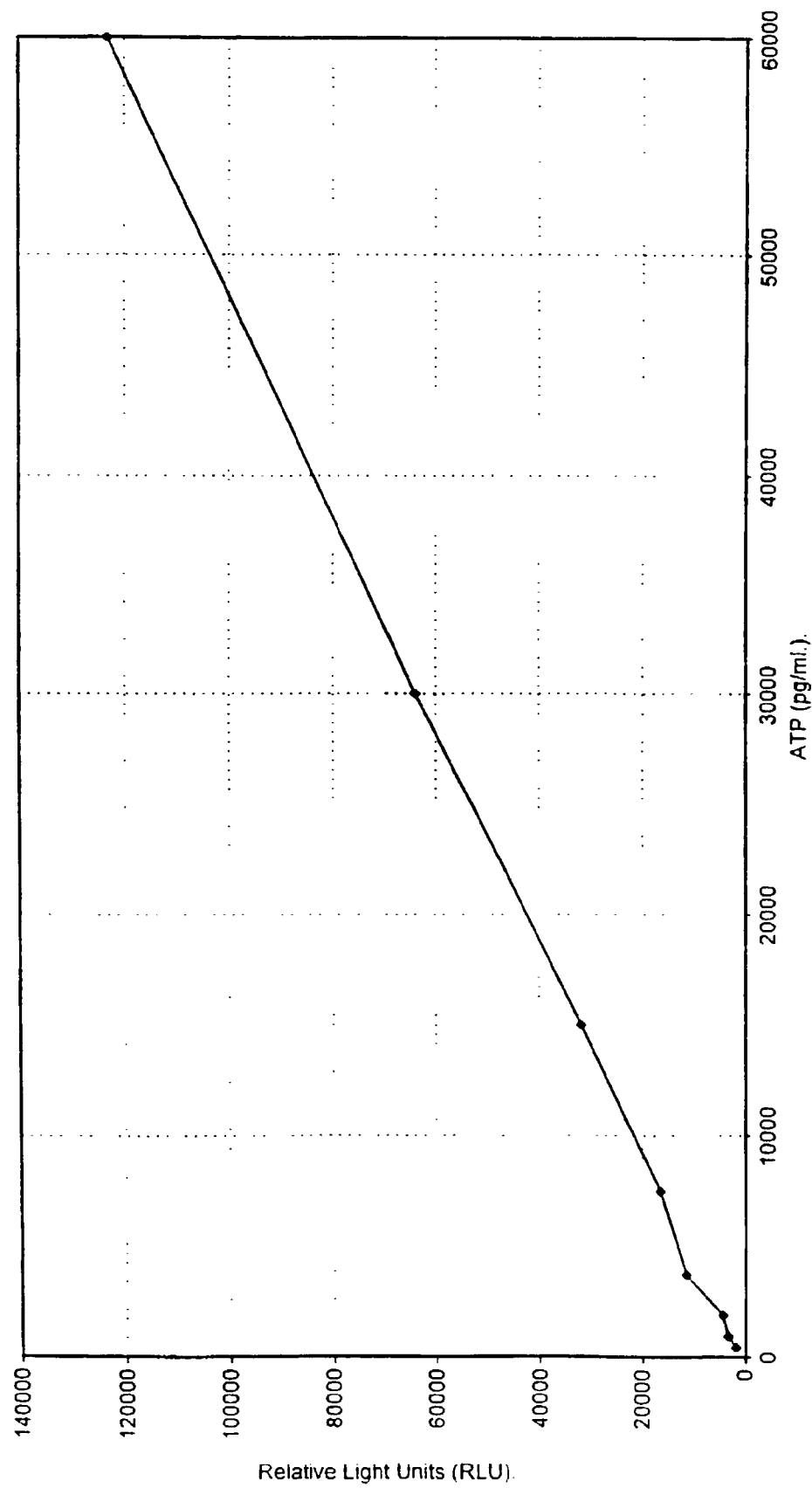
FIG. 11 is a graph showing the relationship between the concentration of ATP (pg/ml) and the intensity of chemiluminescence (RLU) for different concentrations of ATP.
Figure 12:
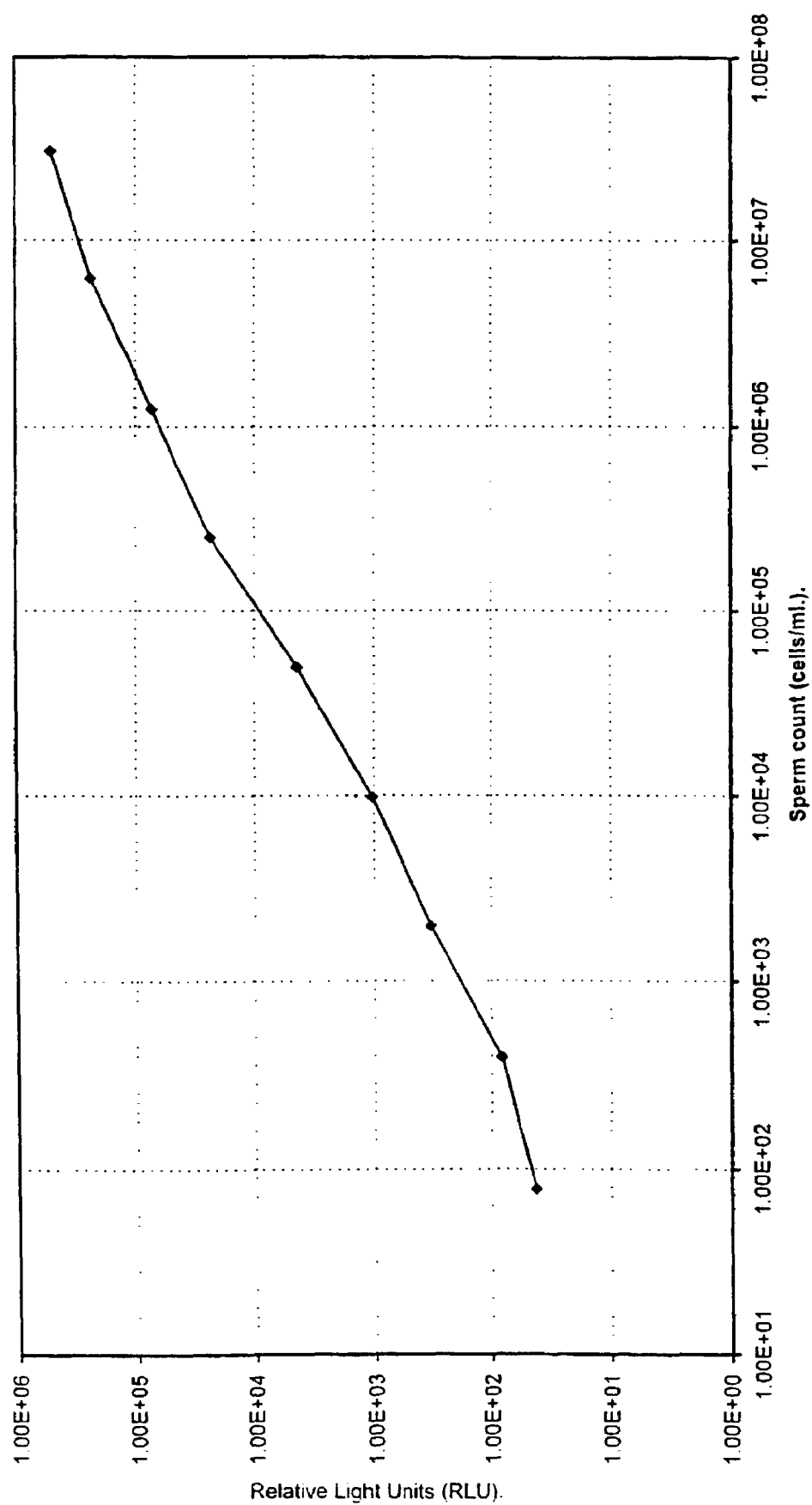
FIG. 12 is a graph showing ATP concentration against bovine sperm count for bull A.

Using FIG. 3 and FIG. 11 the ATP concentration per sperm for bulls A and B can be calculated (13.5.97). These sperm samples were 24 hours old at the time of the estimation of ATP content.

For bull A, at a dilution rate of 1:125, the total sperm count was 1,240,000 cells/ml. and the bioluminescence was 73659 RLU (FIG. 3).

From FIG. 11 (relationship between ATP concentration and RLU), a value of 73659 RLU corresponds to an ATP concentration of 34286 pg/ml.

Therefore 1,240,000 sperm contained 34286 pg of ATP=0.02765 pg/sperm or 2.765 ug ATP/$10^8$ sperm.

1 nanomole (nM) of ATP=505 ng ATP.

Therefore 2765 ng ATP/$10^8$ sperm=5.475 nM ATP/$10^8$ sperm.

The live:dead ratio of FFE prepared sperm for bull A was 82%.

The ATP content was therefore 5.475×100/82=6.68 nM ATP/$10^8$ live sperm.

The corresponding figure for bull B (81% live) was 13.41 nM ATP/$10^8$ live sperm.

For bull B on 11.6.97 after 48 hours incubation (FIG. 4 and FIG. 11) the live:dead ratio was only 15%. The ATP content was 5.72 nM/$10^8$ live sperm.

FISH Analysis

Gledhill (1983) and Amman (1989) suggest the use of DNA probes that specifically bind to selected sites on the X or Y chromosomes to positively identify individual sperm. Fluorescent molecules can be deposited in chromatin at the sites of specific DNA sequences by use of fluorescence in situ hybridisation (FISH). DNA or RNA sequences are first labelled with reporter molecules. The probe and the target chromosomes or nuclei are denatured. Complementary sequences in the probe and target are then allowed to reanneal. After washing and incubation in fluorescently labelled affinity reagents, a discrete fluorescent signal is visible at the site of probe hybridisation (Trask 1991).

Preparation of Slides

Separated samples were taken from the extremes of the collection range as determined by bioluminescence and shown in the results tables 17 to 19, (FIGS. 5 to 7). Four samples were taken from each end of the collection range corresponding as close as possible to RLU readings of 500, 1000, 2000 and 4000. This was done to maximise as far as possible the chances of completing a full FISH analysis for each bull at the extremes of the collection range.

Each slide prepared for FISH was loaded with a 10 µl drop of separated sperm and a 2 µl drop of unseparated (control) sperm taken from the Triethanolamine washed final sample prepared for FFE but prior to FFE. The position of each drop was marked on the slide by using a diamond pen. Thus each slide prepared for FISH carried marked samples of control (unseparated) and separated sperm for each individual ejaculate from each bull.

At the extremes of the FFE separation range, the practical experimental difficulties inherent in successfully transferring small numbers of separated cells from an FFE collection vessel to a 10 µl drop on a slide for FISH analysis were considerable. It is likely that cells were lost by sticking to the sides of pipettes and containers. In addition to this potential source of experimental failure, the FISH process when performed on such prepared slides was not guaranteed to produce a signal, especially when using an experimentally prepared probe as was the case in this project. It was essential therefore, to provide sufficient separated sperm for analysis whilst at the same time allowing for sperm losses during handling coupled with hybridisation failure.

Slides prepared as above were then allowed to air dry and then immediately placed in methanol:glacial acetic acid (3:1) (Fisher Scientific, Loughborough, England), and stored in a freezer at −20° C. for 17 hours (overnight) for fixing. The slides were then removed and incubated for 5 minutes in fresh fixative at room temperature, air dried and put through an ethanol series of 70%, 100%, 100% ethanol (Fisher Scientific, Loughborough, England), for 5 minutes at each step. Slides were then stored in a sealed box containing silica gel at −20° C. until needed for FISH.

Preparation of Probes

A bovine Y-chromosome specific probe was used to perform the FISH analysis.

The Y-probe was supplied by the laboratory of Professor Ingemar Gustavsson, Swedish University of Agricultural Sciences, Uppsala, Sweden.

All the FISH analysis performed during this project was done at the laboratory of Professor Joy Delhanty, The Human Genetics Group, University College, Wolfson House, 4 Stephenson Way, London NW12HF.

The micro-dissected bovine Y-specific DNA probe was amplified to enhance stocks by using the Degenerate Oligonucleotide-Primed PCR (DOP PCR) as described by Telenius et.al. (1992).

The first round of DOP PCR was performed as follows:

DOP PCR I. (Hybaid Omnigene TR3 CM220).

| PCR mix | Volume |
|---|---|
| DNA sample (from original probe suspension) | 2 µl. |
| 10 × Taq buffer (HT Biotechnology, UK). | 5 µl. |
| 2 mM dNTP's. (Pharmacia, UK). | 5 µl. |
| DOP primer (0.1117 nmols/µl.). (Oswel DNA services, Southampton, UK). | 0.9 µl. |
| Taq (5 units/µl) (HT Biotechnology, UK). | 0.5 µl. |
| H₂O. | 36.6 µl. |
| Overlay with mineral oil (Sigma, UK). | |

| PCR programme | | |
|---|---|---|
| 94° C. | 9 mins. | × 1 cycle. |
| 94 | 1 min. | } |
| 30 | 1.5 min. | }× 3 cycles. |
| 72. | 3 min. | } |
| 94 | 1 min. | } |
| 62 | 1 ... | }× 25 cycles. |
| 72 | 1.5 ming. | } |
| 72 | 8 mins. | × 1 cycle. |

The second round of DOP PCR was performed to incorporate a rescent label into the Y-probe using rhodamine red (fluorored, Amersham, UK).

DOP II (labelling). (Hybaid Omnigene TR3 CM220).

| PCR Mix | Volume |
|---|---|
| DOP I amplified DNA | 5 µl. |
| 10 × Taq buffer. | 5 µl. |
| dNTPs (2 mM: dATP, dGTP, dCTP. 1 mM dTTP). | 5 µl. |
| DOP primer (0.1117 nmoles/µl). | 0.9 µl. |
| Taq (5 units/µl). | 0.4 µl. |
| Label (rhodamine red). | 2.5 µl. |
| H₂O. | 31.2 µl. |
| Overlay with mineral oil. | |

| PCR Programme. | | |
|---|---|---|
| 94° C. | 5 mins. | × 1 cycle. |
| 94 | 1 min. | } |
| 62 | 1 min. | }× 25 cycles. |
| 72 | 1.5 mins. | } |
| 72 | 8 mins. | × 1 cycle. |

After the DOP II protocol, PCR labelled product could be seen as a stained dot at the bottom of the eppendorf tubes if the labelling/amplification had worked. Labelled product was stored at −20° C. until needed.

Precipitation of DNA

Five microlitres of DOP PCR labelled product was transferred to a 0.5 ml. eppendorf tube. To this was added: 4 µl. of denatured herring sperm (or salmon sperm) DNA (10.1 mg/ml., Sigma, UK).

One tenth volume of Na. Acetate (3M, pH 5.5), (BDH, UK). i.e. 0.9 µl.

2 volumes of ethanol=19.8 µl. of 100% ethanol (Fisher, UK).

The solution was then mixed well and held at −20° C. overnight or −70° C. for 1.5 hours to precipitate the DNA. (The precipitation is needed so that all surplus reagents from the PCR product can be removed [including surplus fluorochrome], to give closer control of probe volume and concentration when formulating the hybridisation mix/probe suspension later on in the protocol).

The solution was then removed from the freezer and centrifuged at 250 g for 20 mins. in a microfuge to condense the DNA into a distinct pellet.

The supernatant was then poured off and the eppendorf inverted on a paper towel to drain off the remaining supernatant. Finally, a Gilson pipette was used to suck out any residual supernatant.

The pellet was then freeze dried before suspending in the hybridisation solution.

Fluorescence In Situ Hybridisation (FISH)

Day One

All previously prepared slides containing sperm were removed from storage at −20° C. and put through an alcohol series of 70%:90%:100% ethanol for 5 mins each to ensure complete dehydration, and air dried.

Denaturing of Sperm/Metaphase DNA

All sperm and metaphase prepared slides were incubated for 20 minutes in 3M NaOH (BDH, UK) at room temperature, followed by dehydration in 70%, 100% and 100% ethanol for 5 minutes each. The slides were then allowed to air dry.

Denaturing of Probes

Hybridisation mix was made up as follows:

Fifty percent formamide (BDH, UK).

2×Saline Sodium Citrate (SSC). Taken by diluting 1:10 from a 20×SSC stock consisting of 175.3 g NaCl (BDH, UK), 88.2 g Na Citrate (BDH, UK) in 1 litre of water and adjusted to pH 7.0 with concentrated HCl (BDH, UK).

10% Dextran Suphate (BDH, UK).

Ten µl of the above solution was added to each freeze dried pellet of labelled DNA in a 0.5 ml. eppendorf tube (see precipitation of DNA) and left for 20 minutes at 4° C. The solution was then mixed thoroughly using a Gilsson pipette. Aliquots of hybridisation mix were either used fresh, or stored at −20° C. until needed.

Each 10 µl. sample of hybridisation mix was denatured for 10 mins at 75° C. in a PCR machine. The eppendorf tubes containing the denatured probe in the hybridisation mix were then placed in a polystyrene rack in a waterbath at 37° C. until needed.

Ten microlitres of the probe suspension was applied evenly to a clean glass coverslip. The denatured slide preparation was then applied to the coverslip ensuring an even coverage of the probe suspension over the sample area.

Slides were then sealed with cow gum (Cowproofings Ltd., Slough, Berks, UK) and hybridised in a humidified chamber at 37° C. for 24 hours.

Day Two

Coverslips were removed with tweezers from the hybridisation slide samples. In order to avoid damping of the fluorescence signal, from this point on all slides were kept out of the light as much as possible. When in the waterbath, the lid was kept on. When on the bench, silver foil coated plastic beakers were used to cover the Coplin jars.

The samples were then washed in a denaturing agent (50% formamide and 2×SSC) in order to remove non-specifically bound probe. Three washes were performed at 45° C. for 5 minutes per wash, followed by 3 washes in 2×SSC of 5 mins each at 45° C. All formamide washes were performed in a fume cupboard.

All slides were then washed for 10 minutes in TNT, made up as follows:

TN=1M Tris (121.14 g/litre) (Tris[hydroxymethyl]aminomethane hydrochloride, BDH, UK); plus 1.5M NaCl (87.66 g/litre. BDH, UK) in 1 litre of distilled $H_2O$ at pH 7.5.

TNT=1×TN+0.05% Tween 20 (Sigma, UK)=100 ml 1×TN+25 µl. Tween 20.

Slides were then washed for 10 minutes in water and put through a 70-90-100% alcohol series for 5 mins. per step. (This alcohol series is to totally dry each slide so that an "antifade" solution can be applied to prevent the flourochromes from fading).

The slides were then mounted in an "antifade" solution (Vectashield, Vector Labs, Burlingame, Calif., USA) by placing a drop of "antifade" (1 ml. of Vectashield plus 4 µl. 0.2 mg/ml 4,6,-diamidino-2 phenylindole or DAPI; Sigma, UK) on a coverslip and picking this up with the slide. Mounted slides were stored at 4° C.

For analysis, slides were viewed under a fluorescence microscope (Zeiss Axioskop, Germany) linked to a computer enhanced imaging system (Kaf 1400 plus Smart Capture Analysis; Vysis, UK).

Final Results

Following the optimisation of the FFE process, a total of 26 semen samples were subjected to FFE, 13 from each of the two bulls Luke and Inquiry. Of these separation runs, the first 3 from each bull were made to re-check the optimisation of the FFE machine, and the next 10 from each bull were sampled for separated sperm within the detectable extremes at each end of the separation range.

Four slides were prepared from each end of the separation range for each semen sample and stored for FISH analysis, a total of 8 slides per separated sample. In all therefore, 80 slides were prepared from each bull, a total of 160 slides prepared for FISH analysis.

FISH analysis was subsequently performed on 80 of these slides (40 from each of five FFE separation runs from each bull), of which 22 (27.5%) produced a fluorescent signal. The FISH results obtained from these successfully hybridised and FFE separated samples are shown in FIG. 8. Insufficient time was available to examine the remaining 80 slides, which were placed in storage at 5° C. in light proof boxes. Four of these remaining slides were examined in the laboratories of UNCEIA, Maisons-Alfort, France, where bovine X and Y-chromosome specific probes were used to perform a FISH analysis. The results of this analysis are shown in FIG. 9.

Only three FFE separation runs were found to produce slides that hybridised successfully from either one or both bulls. These runs were made on 30.7.98, 5.8.98 and 3.9.98. The FFE separation profiles for these runs are shown in tables 17 to 19 and FIGS. 21 to 23 respectively. No FFE separation data has been included in the results for separated samples that failed to hybridise during the FISH process.

The FISH results can be summarised as follows:

FISH analysis was performed on a total of 84 slides thought to contain separated sperm. The following results do not include the 4 slides examined at UNCEIA, who were not prepared to divulge details of their unpublished technique.

Number of slides with an even distribution of a detectable fluorescent signal in the control drop=22 (27.5%).

Number of slides with an uneven distribution of a detectable fluorescent signal in the control drop=13 (16.25%).

Number of slides showing hybridisation failure (no detectable signal)=45 (56.25%).

Number of slides containing no separated sperm=12 (15%).

Number of slides containing separated sperm=68 (85%).

One slide contained no separated or control sperm.

All three FFE separation runs performed on both bulls and yielding a detectable FISH signal, produced separation profiles consistent with previous results achieved during optimisation.

The FISH results from separated samples collected from the anode end of the separation range yielded much lower numbers of separated sperm than achieved at the cathode end of the collection range. It is not known why this occurred.

Statistical Analysis.

Chi-squared statistical analysis was performed on separated samples as compared with controls, where larger numbers of separated sperm were evident. For the sample Luke 69 (26.8.98), which was analysed at UNCEIA, a binomial statistical analysis was made as no control sperm count had been performed. An assumed control count of 50% each for X and Y-bearing sperm was therefore used in the calculation for binomial distribution in this sample.

Sperm Collected from FFE Fractions Towards the Anode

For FFE separated sperm cells collected from fractions towards the anode, in five of the nine separation runs performed, a skew towards putative X-chromosome bearing sperm was present. This included the only FFE separation result obtained from Inquiry. Chi-squared analysis showed that for two of these collection runs from Luke, (where larger numbers of separated sperm were evident) this skew was statistically significant. Six of the separation runs yielded insufficient numbers of separated sperm for statistical analysis, all of which were from Luke. The lab. at UNCEIA (by chance) performed no FISH analysis on sperm fractions collected towards the anode.

The single separation run yielding FISH results from Inquiry produced a non-significant skew towards putative X-bearing sperm.

For all collections from both bulls collected from fractions towards the anode, the total number of separated sperm identified was 137, of which 41 (29.9%) carried a signal (Y-bearing), and 96 (70.1%) did not (putative X-bearing). The totals for the control drops for both bulls showed a distribution of 1473 (51.5%) for cells carrying a signal (Y-bearing) and 1386 (48.5%) for cells carrying no signal (putative X-bearing). This represented a statistically significant skew towards the collection of X-chromosome bearing sperm for separated fractions against controls (unseparated) sperm.

Sperm Collected from FFE Fractions Collected Towards the Cathode (Excluding Samples Analysed at UNCEIA)

For FFE separated sperm collected from fractions towards the cathode, in five of the 13 separation runs performed, a significant skew towards putative X-chromosome bearing sperm was present. This skew was present in two of three samples from Inquiry and three samples from Luke. However, in three separation runs from Luke a significant skew towards Y-chromosome bearing sperm was also present. One separation run from Luke yielded insufficient sperm numbers for statistical analysis.

Of the three separation samples from Luke which showed a significant skew towards Y-bearing sperm, one was one of two samples collected from the separation run made on 30.7.98, and the other two were two of three samples collected from the separation run made on 5.8.98. For both of these separation runs, the sample at the outermost extreme of the cathode collection range contained a skew of X-bearing sperm cells. However, this skew was only significant in the case of the 30.7.98 separation run.

For Inquiry, the total amount of separated sperm showing a skew towards putative X-bearing sperm was significant ($p<0.01$). For Luke the total amount of separated sperm analysed showed a slight but insignificant skew towards putative X-bearing sperm.

For all collections from both bulls collected from fractions towards the cathode, the total number of separated sperm identified was 2207, of which 929 (42%) carried a signal (Y-bearing) and 1278 (58%) did not (putative X-bearing). The totals for the control drops for both bulls showed a distribution of 2105 (48.8%) for cells carrying a signal (Y-bearing) and 2208 (51.2%) for cells carrying no signal (putative X-bearing). This represented a statistically significant skew towards the collection of X-chromosome bearing sperm for separated fractions against controls (unseparated) sperm.

Sperm Samples Analysed at UNCEIA

These slides were analysed as a personal favour and were only done as and when time permitted. A total of 32 slides were sent to UNCEIA for analysis, of which only 4 were used.

All four slides analysed were (by chance) from the cathode end of the separation range, and all showed a significant skew towards X-bearing sperm as compared with unseparated controls. These results were obtained by using both X and Y-specific bovine DNA probes, and therefore represent a positive identification by fluorescent signal for each class of cell.

Although the numbers of sperm analysed at UNCEIA were small, these results support the previous findings for putatively X-bearing sperm separated in FFE fractions towards the cathode.

This project has embraced a novel approach to the separation of X and Y-chromosome bearing sperm based on the hypothesis that sex chromosome linked phenotypic differences exist at the cell surface.

The mechanisms of somatic cell membrane assembly have been reviewed by the following authors (Sabatini et al. 1982, Alberts et al. 1983, Yeagle 1987, Becker and Deamer 1991, and Granner 1993a) and, where appropriate, compared with sperm cell membrane assembly during spermiogenesis (Bellve 1982, and Holt 1982).

The genetic mechanisms that are active in the haploid genome of the developing sperm cell have been reviewed by the following authors (Fujimoto and Erickson 1982, Stern et al. 1983, Distel et al.1984, Hecht 1986, Hecht et al. 1986, Hecht 1987, Handel 1987, Heidaran and Kistler 1987, Silver et al. 1987, Hecht 1990, Wang et al 1990, Cebra-Thomas et al. 1991, Chayko and Martin-Deleon 1992, Mizuki et al. 1992, Winer and Wolgemuth 1993, Eddy et al. 1993, Morales et al. 1994, Penttila et al. 1995, Aho et al. 1996 and Pusch et al. 1996), with particular reference to the sex chromosomes (Koopman et al 1989, Nagamine et al. 1990, Koopman et al. 1991, Handel and Hunt 1992, Eddy et al. 1993, Shannon and Handel 1993, Hendriksen 1993a, 1995, 1996; Calenda 1994, Conway et al. 1994, Reijo et al. 1995, Hargreave et al. 1996, Vogt 1996, Elliot et al 1997, Habermann et al. 1998 and Penfold et al. 1998) providing experimental evidence that demonstrates haploid gene expression at the level of the sex chromosomes during spermatogenesis in several mammalian species.

The role of the Y-chromosome in mammalian spermatogenesis has been reviewed with special reference to the human (Vollrath et al. 1992, Muller 1994 and Vogt et.al. 1997) and the mouse (Gubbay and Lovell-Badge 1994). A large body of evidence is available from studies made in infertile men suffering from Y-chromosome specific microdeletions to suggest that haploid Y-chromosome specific genes are essential for the normal development of sperm morphology and fertility, and in particular the DAZ and RBM gene clusters (Ma et al. 1992, Reijo et al. 1995, Hargreave et al. 1996 and Kremer et al. 1997).

Given that the Y-chromosome must act in a haploid manner in mammalian species such as the human and the mouse in order for spermiogenesis to proceed normally, then the role of intercellular bridges (Dym and Fawcett 1971), during spermiogenesis in such species must now be beyond question. Clearly, X-chromosome bearing sperm could not develop normally without the haploid genetic controls imposed by their Y-chromosome bearing neighbours being successfully transmitted within the spermatogenic cell syncytium.

There is a certain amount of evidence to suggest that natural sex ratios in mammalian species can be affected by phenomena such as meiotic drive and transmission ratio distortion (Ohno et al. 1963, Gropp et al. 1976, Gileva 1987, Hurst and Pomianski 1991 and Lyttle 1993).

The phenomenon of genomic imprinting may also involve genetic events during spermiogenesis (Barlow 1995, Forejt et al. 1995, and Lyon 1995) that could theoretically produce slightly different phenotypes between X and Y-chromosome bearing sperm, and which are X-chromosome mediated.

The technique of Free-Flow Electrophoresis (FFE) has been used repeatedly by previous workers to produce differing degrees of X and Y-chromosome sperm separation in mammalian species (Kaneko et al. 1983, 1984, Mohri et al. 1986, Engelmann et al. 1988, Ishijima et al. 1991, 1992, Manger et al. 1992, Blottner et al. 1994 and Manger et al. 1997). However, much of this work has involved the use of sperm samples which will have compromised separation results due to surface charge effects resulting from cell senescence (Mann and Lutwak-Mann 1981, 1981a; Nissen and Kreysel 1983, Miesel et al. 1993, Aitken 1995), accessory coatings (Yanagimachi et al. 1972, Moore 1979, 1995; Hammerstedt and Parks 1987, Myles 1993, Eddy 1994, Eddy and O'Brien 1994 and Yanagimachi 1994) and capacitation (Austin 1951, Chang 1951, Bedford 1983, Langlais and Roberts 1985, Burkmann 1995 and Frazer 1995, 1995a) in a population of cells that is naturally highly heterogenous (Bedford 1983 and Cummins 1995). Similarly, FFE efficiency will have been compromised by the use of unreliable machines in earlier work (Weber, personal communication, 1995) or by the effects of galvanotaxis (sperm migration through inherent sperm motile activity within the FFE separation chamber), when separation chamber temperatures are above 10° C. (Bangham 1961, Meistrich 1982, Manger et al. 1992, 1997; Blottner et al. 1994).

In this project, the effects of cell senescence, accessory coatings and the acrosome reaction have been minimised by incubating all semen samples used for the project in TEST-Yolk, a diluent which reduces rates of cell senescence whilst at the same time preserving most of the live sperm in the sample in a capacitated, but not acrosome reacted state (Bolanos 1983, Johnson et al. 1984, Ijaz and Hunter 1988, 1989; Ijaz et al 1989 and Iqbal and Hunter 1995a, 1995b, 1995c). The effects of galvanotaxis have been completely removed by using a temperature of 5° C. in the separation chamber, thus ensuring that all sperm are immotile during the FFE process (Manger et.al. 1992, Blottner et.al. 1994).

It is hypothesised in the current study that sperm preserved in TEST-Yolk as above form a much more homogenous cell sample, and due to the removal of accessory coatings during the capacitation process accompanying incubation in TEST-Yolk, one which could more closely resemble sperm populations at spermiation than has ever been previously studied in FFE. If this has in fact been the case, then the molecular nature of the cell surface in a population of cells so treated, may be a more genuine reflection of the cell surface as assembled by the haploid genome, than any other sperm sample previously studied using FFE or any other cell surface technology.

If the above assumption is correct, then it is a logical extrapolation to expect the maximum FFE induced differences in cell surface within the separated population to exist at the extremes of the separation range. In this project, the FFE optimisation results showed that bovine sperm cells could be repeatably and consistently isolated from the extremes of the FFE separation range. What is more, the populations so detected at the separation extremes represented a significantly small proportion of the total ejaculate (0.02%), and one which had never been studied in isolation before.

Cells recovered from FFE collection fractions at the extremes of the separation range were fixed on microscope slides and analysed using a FISH procedure incorporating a micro-dissected Y-specific bovine DNA probe (Hassaname et al. 1998). This technique has only been successfully reported once previously in bovine sperm, and never before for use in the verification of sex ratio in purportedly separated bovine sperm samples. A hybridisation success rate of 27.5% was achieved for all FFE separated samples analysed using this micro-dissected Y-chromosome specific DNA probe.

A success rate of this order for the initial use of an experimental probe is considered perfectly acceptable by Wells (1998, personal communication) and McDermott (1998, personal communication) in the human cytogenetics laboratories at University College London, and the Southmead Hospital Trust, Bristol respectively.

Notwithstanding the lack of time available to fully optimise the use of the Y-specific bovine probe used in this experiment, we are fully confident of the authenticity of the results achieved in slides where a uniform signal was present in the control population. In all cases, separated and control drops were prepared adjacent to each other on a single slide. For each slide, both control and separated drops were subjected to all laboratory procedures at exactly the same time, including the FISH analysis which was performed with both drops under a single cover slip. Throughout each step of the FISH procedure therefore, all cells from both control and separated drops were experimentally treated as a single population. There was no possibility that a slide displaying an even distribution of a positive fluorescent signal throughout the control drop, should not have displayed a similar distribution of signal throughout the separated drop (assuming of course a nil effect of FFE in the separated drop).

At the anode extreme of the FFE separation range (maximum negative cell surface charge), a combined total of 137 cells from both bulls were analysed of which 41 (29.9%) were Y-bearing and 96 (70.1%) were putative X-bearing. At the cathode extreme of the FFE separation range (minimum negative cell surface charge), a combined total of 2207 cells from both bulls were analysed of which 929 (42%) were Y-bearing and 1279 (58%) were putative X bearing. Chi-squared statistical analyses showed that the levels of putative X-bearing cell enrichment at both ends of the separation range were significant ($p<0.1$).

These preliminary results strongly suggest that the bovine sperm samples treated and analysed in this project have been successfully separated according to differences based on sex-chromosome linked cell surface charge effects. There are therefore grounds for concluding that charge sensitive compositional differences exist at the level of the sperm plasmalemma between X and Y-chromosome bearing bovine sperm. This being the case, the mechanisms involved in the creation of these structural differences must be as a result of sex-chromosome linked haploid gene expression.

The fact that an enrichment of X-chromosome bearing cells was identified at each end of the separation range was not expected. However, given the apparent importance of several specific domains within the Y-chromosome in the establishment of normal sperm morphology including head shape, this is not particularly surprising. For any given Y-specific gene product that is incorporated into the sperm membrane, it would be logical to assume that the cells most likely to show a quantitative difference in the levels of incorporation of such a product, would be X-bearing. This would reflect the increased difficulties for consistent and repeatable Y to X-bearing cell transfer and membrane incorporation of these essential products into X-bearing cells, in comparison with incorporation of such products into the plasmalemma of the Y-bearing cell of origin. It is the X-chromosome bearing cells within the spermatogenic cell syncitium that are more likely to be slightly depleted in essential Y-bearing products, whatever their nature.

The separation results achieved in this project would simply suggest that at least two Y-chromosome specific gene products are incorporated at the cell surface, but that one is positively and the other negatively charged. Hence, an X-bearing cell deficient in levels of the more negatively charged product (or products) would accumulate at the cathode end of the separation range (lower overall cell surface negative charge), whilst an X-bearing cell more deficient in the more positively charged product (or products) would accumulate at the anode end of the range (greater overall cell surface negative charge). It is likely that the result achieved in this project represents phenotypic differences in the distribution of Y-chromosome specific gene products at the sperm cell surface, and that such products vary considerably in their degree of surface charge.

For sperm cells collected from FFE fractions towards the cathode end of the separation range, there were some contradictory findings. For Luke, three such collection fractions showed a significant degree of skew towards Y-chromosome bearing sperm, whilst three showed a significant degree of skew towards X-chromosome bearing sperm. Both X and Y-chromosome bearing sperm enrichment appeared within the same separated sample for 2 of the 3 samples analysed for this bull at this end of the range. However, for both of these samples, the collection fraction analysed at the outer extreme of the collection range, did contain a skew towards putative X-bearing cells which was significant in one case.

It would appear from these rather contradictory results that at the cathode end of the collection range for this bull, there may be small populations of cells which are both X and Y-chromosome enriched. For Luke samples separated on 30.7.98, fraction 51 contained a significant skew towards Y-bearing sperm and fraction 52 a significant skew towards putative X-bearing sperm. For samples separated on 5.8.98, fractions 44 and 52 produced a significant skew towards Y-bearing sperm, and fraction 54 an insignificant skew towards X-bearing sperm.

In considering fractions 51 and 52 for 30.7.98 and fractions 52 and 54 for 5.8.98, it would appear that distinct populations of X and Y-chromosome bearing sperm (as identified by FISH analysis on each fraction), share very similar surface charge properties as determined by their equally similar FFE migration profiles. It is difficult to see how differences in haploid gene expression could be responsible for this effect. If cell surface charge properties are in fact similar between X and Y-chromosome bearing sperm, then it follows that minimal sperm enrichment of X or Y-chromosome bearing sperm should exist between closely apposed FFE collection fractions. This finding is therefore contradictory and begs the question as to how such sperm enrichment was achieved. It would appear that either some sex-chromosome linked effect is active during the FFE process that is not charge sensitive, or that this is simply a spurious result.

Sperm were incubated in TEST-Yolk for 24 hours at 5° C. overnight prior to FFE, and the FFE machine was held at 5° C. to ensure that all sperm were immotile. It is therefore not possible that any sex chromosome linked effects due to "galvanotaxis" could account for this difference. The only other factor that could theoretically effect sperm migration during FFE is sex chromosome related differences in weight. However, this has already been ruled out as a potential detectable difference between sperm of different sex chromosome bearing class, as weight differences within class are likely to be much greater for any given population of sperm (Meistrich 1982, Gledhill 1988 and Johnson 1994).

Alternatively, if these apparent differences in sperm surface charge between adjacent or closely apposed FFE collection fractions are due to differences in sex chromosome linked haploid gene expression, what is the genetic mechanism responsible for this? It is unlikely to be as a result of the X-chromosome bearing cells within the spermatogenic cell syncitium being slightly more depleted in essential Y-bearing products as described previously. Such differences in membrane composition, if charge sensitive, would tend to become more apparent only at the extremes of the electrophoretic separation range where maximum difference in surface charge exists. Between closely aligned FFE collection fractions where surface charge differences are minimal, any charge sensitive Y-chromosome specific gene product incorporation should be similar in both X and Y-bearing cells, and consequent enrichment by class should not be significant. All the available evidence would suggest that this is therefore a spurious result.

Sperm identified as "putative X-bearing" in this project have only been identified as such by default. A positive identification with an X-specific probe would overcome this difficulty and help to throw new light on these rather contradictory findings.

The results from the laboratory at UNCEIA provide some preliminary data on the question of the authenticity of the "putative" X-bearing cell. Unfortunately, and quite by chance, the samples selected for this FISH analysis were all from the cathode end of the FFE separation range. However, the use of an X-specific bovine DNA probe would appear to confirm the findings for "putative" X-bearing cells identified in separated sperm populations elsewhere in this study, i.e. a significant skew towards X-bearing cells at the cathode extreme of the separation range.

Even though this project has successfully analysed sperm at the extremes of the FFE separation range, the degree of enrichment of X-bearing sperm was relatively low (58% at the cathode with 2207 cells analysed, and 70.1% at the anode with 137 cells analysed, excluding slides sent to UNCEIA). The numbers of separated cells available for FISH analysis may have been affected by experimental inefficiencies in the collection of separated cells, and the relatively low success rate of the hybridisation technique at 27.5%.

The collection of cell populations from a separated fraction containing as few as 10,000 cells per ml., and the subsequent transfer of a 10 µl drop of this suspension to a microscope slide for FISH analysis was difficult to perform. It is quite likely that cells would have been lost during this process by sticking to the sides of pipettes and containers. This could have accounted for the low number of cells found in some of the separated samples. Consequently, the numbers of separated cells available for FISH analysis would have been reduced.

The FISH results from separated samples collected at the anode end of the separation range yielded much lower numbers of separated sperm than achieved at the cathode end of the separation range. It is not known why this should be so as the RLU values used to identify collection fractions for sampling were of the same order at each end of the separation range. The sperm densities in all samples prepared for FISH analysis should therefore have been similar (10,000+sperm per ml.). This finding could simply be a result of failure to fully optimise sperm handling and subsequent FISH analysis.

The relatively low hybridisation success rate of 27.5% has been caused by the fact that there was not time during the experimental work to fully optimise the FISH process. Small differences in reaction conditions during each FISH analysis could easily have accounted for this low figure. For example, in some slides, part of the field appeared to be hybridised whilst other areas did not. In these cases failure to suspend the probe evenly in the hybridisation mix could have accounted for these differences. In practice, the low hybridisation rate meant that four slides per bull from each end of the separation range had to be analysed in order to maximise the chances of locating cells from the separation extremes. The results so achieved were therefore not necessarily from the slides at the most extreme ends of the range. This in turn may have affected the degree of enrichment of X-bearing cells as reported in the results.

In cattle, the use of FFE sperm separation in conjunction with an ICSI system could be justified if applied to a trans vaginal system of oocyte recovery as reported by Kruip et al. (1991) for use in elite pedigree donor cows to produce embryos of pre-determined sex.

In the treatment of male infertility in humans, the ICSI technique has become an established and repeatable procedure (Van Stierteghem et al. 1993a, 1993b and Payne 1995). The results of sperm separation experiments with FFE in humans have shown high levels of enrichment in some cases (Kaneko et al. 1983, 1984; Mohri et al. 1986, Engelmann et al. 1988 and Ishijima et al. 1991), although these results have never been consistently repeated. The use of FISH to identify X and Y-chromosome bearing sperm in the human is an established procedure (Armstrong et al. 1994, Chevret et al. 1994, 1996; Han et al. 1994, Miharu et al. 1994, Wang et al. 1994, Spriggs et al. 1995, Martin and Rademaker 1995, Martin et al. 1996, Spriggs et al. 1996, Dineen et al. 1997).

Although the technique of FFE has previously been used to enrich human sperm samples as mentioned above, it has never been applied at the extremes of the separation range as performed in this project. By modifying the FFE technique and selecting sperm from the extremes of the FFE separation range as performed here, it would be possible to produce a more consistent and reliable skew to X-bearing sperm than previously achieved with FFE.

With modern centrifugation and cell handling techniques, it should be possible to identify FFE separation fractions containing only thousands or even hundreds of cells per ml. Such an approach would allow the analysis of subpopulations of cells within individual ejaculates with potentially even greater phenotypic differences than studied here.

Ultimately therefore, it might be possible to work with human sperm samples at a level of FFE separation based on sex chromosome linked phenotypic differences at the cell surface, to ensure that cells collected at either end of the separation range were 100% X-chromosome bearing. Such cells could then be used in a human ICSI and IVF system to produce female progeny. This could be an invaluable contribution to the elimination of sex-linked genetic disorders in humans where it is often the male who is the clinical sufferer.

The invention claimed is:

1. A method of sorting capacitated mammalian sperm cells, the method comprising the steps of:
   a) collecting the sperm cells to be sorted;
   b) stripping extra-cellular material, adhering to or bathing the cells, with a medium containing egg yolk or derivatives thereof at a concentration of up to 30% volume/volume by incubating said collected cells in said medium for a period of time sufficient to preserve most of the live cells in a capacitated state;
   c) removing the egg-yolk medium and any contamination contained therein from the cells obtained in step b);
   d) washing the cells obtained in step c) to remove any residual egg-yolk medium from the collected cells to produce a composition of capacitated cells stripped free from extra cellular material;
   e) subjecting the composition of capacitated cells from step d) to free-flow electrophoresis.

2. The method of claim 1, wherein steps c) and d) employ a buffer.

3. The method of claim 2, wherein said buffer is an electrophoresis buffer.

4. The method of claim 2, wherein said buffer inhibits or prevents cell agglutination.

5. The method of claim 2, wherein said buffer is a triethanolamine buffer.

6. The method according to claim 1, wherein said free-flow electrophoresis is conducted in a separation chamber with constant electrophoretic conditions throughout the separation chamber.

7. The method according to claim 1, wherein the composition of cells are selected from one or both extreme poles of a separation range.

8. The method according to claim 7, wherein the sorted cells are collected from both of said extreme poles.

9. The method according to claim 1, wherein the surface contamination removed comprises one or more of accessory proteins, secretions added to the sperm cells during the process of cell maturation, secretions added to the sperm cells during the process of cell transport, secretion added to the sperm cells during the process of cell storage within the male reproductive tract, micro-organisms from the male reproductive tract and other contaminants or micro-organisms introduced during ejaculation.

10. The method according to claim 8, wherein the collected cells bear X-chromosomes.

11. A method according to claim 1, wherein said cells are stripped by incubation with said medium for a period of time sufficient to delay cells senescence.

12. A method according to claim 1, wherein said cells are stripped by incubation with said medium for at least 24 hours.

13. A method according to claim 1, wherein said sorting is effected based exclusively on endogenous cell membrane properties.

14. A method according to claim 10, wherein said collected cells are non-motile.

15. A method of performing intra cytoplasmic mammalian sperm injection, said method comprising:
   a) sorting sperm cells according to a method comprising;
      i) collecting the sperm cells to be sorted;
      ii) stripping extra-cellular material, adhering to or bathing the collected cells, with a medium containing egg yolk or derivatives thereof at a concentration of up to 30% volume/volume by incubating said collected cells in said medium for a time sufficient to result in most of the live cells of said collected cells to be capacitated;
      iii) removing the egg-yolk medium and any contamination contained therein from the cells obtained in step ii);
      iv) washing the cells obtained in step iii) to remove any residual egg-yolk medium from the collected cells to produce a composition of capacitated cells stripped free trom extra cellular material;

v) subjecting the composition of capacitated cells from step iv) to free-flow electrophoresis to obtain a population of sorted sperm cells; and b) employing a cell from said population of sorted sperm cells in intra cytoplasmic sperm injection.

16. A method according to claim 15, wherein said employed cell is non-motile.

* * * * *

UNITED STATES PATENT AND TRADEMARK OFFICE
CERTIFICATE OF CORRECTION

| | |
|---|---|
| PATENT NO. | : 7,276,329 B2 |
| APPLICATION NO. | : 10/221241 |
| DATED | : October 2, 2007 |
| INVENTOR(S) | : Ian Cumming |

Page 1 of 1

It is certified that error appears in the above-identified patent and that said Letters Patent is hereby corrected as shown below:

Col. 22, Claim 15 line 67: Delete "trom" and replace it with --from--.

Signed and Sealed this

Fifteenth Day of July, 2008

JON W. DUDAS
*Director of the United States Patent and Trademark Office*